United States Patent
Liu et al.

(10) Patent No.: US 9,771,574 B2
(45) Date of Patent: Sep. 26, 2017

(54) APPARATUS FOR CONTINUOUS DIRECTED EVOLUTION OF PROTEINS AND NUCLEIC ACIDS

(71) Applicant: President and Fellows of Harvard College, Cambridge, MA (US)

(72) Inventors: David R. Liu, Lexington, MA (US); Kevin Michael Esvelt, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/704,226

(22) Filed: May 5, 2015

(65) Prior Publication Data
US 2015/0275202 A1   Oct. 1, 2015

Related U.S. Application Data

(63) Continuation of application No. 13/062,098, filed as application No. PCT/US2009/056194 on Sep. 8, 2009, now Pat. No. 9,023,594.

(60) Provisional application No. 61/094,666, filed on Sep. 5, 2008.

(51) Int. Cl.
C12N 15/10   (2006.01)
C12N 7/00    (2006.01)

(52) U.S. Cl.
CPC ..... *C12N 15/1058* (2013.01); *C12N 15/1024* (2013.01); *C12N 15/1037* (2013.01); *C12N 7/00* (2013.01)

(58) Field of Classification Search
None
See application file for complete search history.

(56) References Cited

U.S. PATENT DOCUMENTS

| | | | |
|---|---|---|---|
| 5,223,409 A | 6/1993 | Ladner et al. | |
| 5,658,727 A | 8/1997 | Barbas et al. | |
| 5,712,089 A | 1/1998 | Borrebaeck et al. | |
| 5,821,047 A | 10/1998 | Garrard et al. | |
| 5,965,124 A | 10/1999 | Feinberg et al. | |
| 6,156,509 A | 12/2000 | Schellenberger | |
| 6,429,298 B1 | 8/2002 | Ellington et al. | |
| 6,969,731 B1 | 11/2005 | Tang et al. | |
| 9,023,594 B2 | 5/2015 | Liu et al. | |
| 9,394,537 B2 | 7/2016 | Liu et al. | |
| 2002/0132327 A1 | 9/2002 | Hay et al. | |
| 2003/0119764 A1 | 6/2003 | Loeb et al. | |
| 2003/0203480 A1 | 10/2003 | Kovesdi et al. | |
| 2005/0019753 A1 | 1/2005 | Kukolj et al. | |
| 2008/0220502 A1 | 9/2008 | Schellenberger et al. | |
| 2009/0227463 A1 | 9/2009 | Reif et al. | |
| 2009/0300777 A1 | 12/2009 | Nakayama | |
| 2011/0177495 A1 | 7/2011 | Liu et al. | |
| 2013/0059931 A1 | 3/2013 | Petersen-Mahrt et al. | |
| 2013/0117869 A1 | 5/2013 | Duchateau et al. | |
| 2013/0345065 A1 | 12/2013 | Hassibi et al. | |
| 2014/0201858 A1 | 7/2014 | Ostertag et al. | |
| 2015/0056177 A1 | 2/2015 | Liu et al. | |
| 2016/0348096 A1 | 12/2016 | Liu et al. | |
| 2017/0009224 A1 | 1/2017 | Liu et al. | |
| 2017/0029473 A1 | 2/2017 | Liu et al. | |

FOREIGN PATENT DOCUMENTS

| | | |
|---|---|---|
| WO | WO 90/02809 A1 | 3/1990 |
| WO | WO 91/17271 A1 | 11/1991 |
| WO | WO 92/01047 A1 | 1/1992 |
| WO | WO 92/09690 A2 | 6/1992 |
| WO | WO 92/15679 A1 | 9/1992 |
| WO | WO 92/18619 A1 | 10/1992 |
| WO | WO 92/20791 A1 | 11/1992 |
| WO | WO 93/01288 A1 | 1/1993 |
| WO | WO 9604403 A1 | 2/1996 |
| WO | WO 98/32845 A1 | 7/1998 |
| WO | WO 00/71694 A1 | 11/2000 |
| WO | WO 01/05950 A2 | 1/2001 |
| WO | WO 01/61049 A1 | 8/2001 |
| WO | WO 2005/081632 A2 | 9/2005 |
| WO | WO 2007/066923 A1 | 6/2007 |
| WO | WO 2008/005529 A2 | 1/2008 |
| WO | WO 2009/082488 A2 | 7/2009 |
| WO | WO 2009/108180 A2 | 9/2009 |
| WO | WO 2010/028347 A2 | 3/2010 |
| WO | WO 2011/147590 A2 | 12/2011 |
| WO | WO 2012/088381 A2 | 6/2012 |
| WO | WO 2014/039585 A2 | 3/2014 |
| WO | WO 2014/157820 A1 | 10/2014 |
| WO | WO 2014/158593 A1 | 10/2014 |

OTHER PUBLICATIONS

International Search Report and Written Opinion for PCT/US2015/012022, mailed Sep. 25, 2015.

Carlson et al., Negative selection and stringency modulation in phage-assisted continuous evolution. Nat Chem Biol. Mar. 2014;10(3):216-22. doi: 10.1038/nchembio.1453. Epub Feb. 2, 2014.

Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.

International Preliminary Report on Patentability for PCT/US2015/012022 mailed Aug. 4, 2016.

(Continued)

*Primary Examiner* — Nicole Kinsey White

(74) *Attorney, Agent, or Firm* — Wolf, Greenfield & Sacks, P.C.

(57) ABSTRACT

Aspects of the disclosure relate to an apparatus for continuous directed evolution of a gene of interest. In some embodiments, the apparatus comprises a cellstat and a turbidostat. In some embodiments, the apparatus is useful in methods of passing a nucleic acid from cell to cell in a desired function-dependent manner.

21 Claims, 11 Drawing Sheets

(56) References Cited

OTHER PUBLICATIONS

International Search Report and Written Opinion for PCT/US2015/057012 mailed Jun. 10, 2016.
Ostendorf et al., Characterization of a dam mutant of Serratia marcescens and nucleotide sequence of the dam region. J Bacteriol. Jul. 1999;181(13):3880-5.
Extended European Search Report for EP EP 09812363, mailed Mar. 30, 2012.
International Search Report and Written Opinion for PCT/US2009/056194, mailed Jun. 21, 2010.
International Preliminary Report on Patentability for PCT/US2009/056194, mailed Mar. 17, 2011.
Invitation to Pay Additional Fees for PCT/US2011/066747, mailed Aug. 30, 2012.
International Search Report and Written Opinion for PCT/US2011/066747, mailed Oct. 30, 2012.
International Preliminary Report on Patentability for PCT/US2011/066747, mailed Jul. 4, 2013.
Akopian et al., Chimeric recombinases with designed DNA sequence recognition. Proc Natl Acad Sci U S A. Jul. 22, 2003;100(15):8688-91. Epub Jul. 1, 2003.
Armstrong et al., Chapter 3. Vectors for Phage Display. In: Phage Display of Peptides and Proteins. Kay et al., eds. Academic Press. San Diego, CA. 1996:35-53.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Bloom et al., Evolving strategies for enzyme engineering. Curr Opin Struct Biol. Aug. 2005;15(4):447-52.
Boersma et al., Selection strategies for improved biocatalysts. FEBS J. May 2007;274(9):2181-95.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Caldwell et al., Randomization of Genes by PCR Mutagenesis. PCR Methods Applic. 1992;2:28-33.
Camps et al., Targeted gene evolution in Escherichia coli using a highly error-prone DNA polymerase I. Proc Natl Acad Sci U S A. Aug. 19, 2003;100(17):9727-32. Epub Aug. 8, 2003.
Chasteen et al., Eliminating helper phage from phage display. Nucleic Acids Res. 2006;34(21):e145. Epub Nov. 6, 2006.
Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Information theory based T7-like promoter models: classification of bacteriophages and differential evolution of promoters and their polymerases. Nucleic Acids Res. Oct. 31, 2005;33(19):6172-87. Print 2005.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Corey et al., Trypsin display on the surface of bacteriophage. Gene. Jun. 15, 1993;128(1):129-34.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in Escherichia coli K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Drake, A constant rate of spontaneous mutation in DNA-based microbes. Proc Natl Acad Sci U S A. Aug. 15, 1991;88(16):7160-4.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. Epub Apr. 10, 2011.
Fijalkowska et al., Mutants in the Exo I motif of Escherichia coli dnaQ: defective proofreading and inviability due to error catastrophe. Proc Natl Acad Sci U S A. Apr. 2, 1996;93(7):2856-61.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fuchs et al., Targeting Recombinant Antibodies to the Surface of Escherichia Coli: Fusion to a Peptidoglycan Associated Lipoprotein. Bio/Technology. 1991;9:1370-72.
Garrard et al., Fab assembly and enrichment in a monovalent phage display system. Biotechnology (N Y). Dec. 1991;9(12):1373-7.
Gibson et al., Enzymatic assembly of DNA molecules up to several hundred kilobases. Nat Methods. May 2009;6(5):343-5. Epub Apr. 12, 2009.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993;12(2):725-34.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and Escherichia coli expression of a human IgM Fab. Hum Antibodies Hybridomas. Apr. 1992;3(2):81-5.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Huse et al., Generation of a large combinatorial library of the immunoglobulin repertoire in phage lambda. Science. Dec. 8, 1989;246(4935):1275-81.

(56) References Cited

OTHER PUBLICATIONS

Husimi et al., Cellstat-a continuous culture system of a bacteriophage for the study of the mutation rate and the selection process of the DNA level. Rev Sci Instrum. Apr. 1982;53(4):517-22.

Husimi, Selection and evolution of bacteriophages in cellstat. Adv Biophys. 1989;25:1-43.

Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.

Ikeda et al., In vivo and in vitro activities of point mutants of the bacteriophage T7 RNA polymerase promoter. Biochemistry. Sep. 22, 1992;31(37):9073-80.

Ikeda et al., Selection and characterization of a mutant T7 RNA polymerase that recognizes an expanded range of T7 promoter-like sequences. Biochemistry. Sep. 7, 1993;32(35):9115-24.

Imburgio et al., Studies of promoter recognition and start site selection by T7 RNA polymerase using a comprehensive collection of promoter variants. Biochemistry. Aug. 29, 2000;39(34):10419-30.

Johns et al., The promise and peril of continuous in vitro evolution. J Mol Evol. Aug. 2005;61(2):253-63. Epub Jun. 27, 2005.

Joho et al., Identification of a region of the bacteriophage T3 and T7 RNA polymerases that determines promoter specificity. J Mol Biol. Sep. 5, 1990;215(1):31-9.

Joung et al., A bacterial two-hybrid selection system for studying protein-DNA and protein-protein interactions. Proc Natl Acad Sci U S A. Jun. 20, 2000;97(13):7382-7.

Kawarasaki et al., Enhanced crossover SCRATCHY: construction and high-throughput screening of a combinatorial library containing multiple non-homologous crossovers. Nucleic Acids Res. Nov. 1, 2003;31(21):e126.

Khlebnikov et al., Modulation of gene expression from the arabinose-inducible araBAD promoter. J Ind Microbiol Biotechnol. Jul. 2002;29(1):34-7.

Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.

Kozak et al., Structural features in eukaryotic mRNAs that modulate the initiation of translation. J Biol Chem. Oct. 25, 1991;266(30):19867-70.

Kuzmine et al., Binding of the priming nucleotide in the initiation of transcription by T7 RNA polymerase. J Biol Chem. Jan. 31, 2003;278(5):2819-23. Epub Nov. 9, 2002.

Latimer et al., Specificity of monoclonal antibodies produced against phosphorothioate and ribo modified DNAs. Mol Immunol. Oct. 1995;32(14-15):1057-64.

Lincoln et al., Self-sustained replication of an RNA enzyme. Science. Feb. 27, 2009;323(5918):1229-32. Epub Jan. 8, 2009.

Lindemann et al., Evolution of bacteriophage in continuous culture: a model system to test antiviral gene therapies for the emergence of phage escape mutants. J Virol. Jun. 2002;76(11):5784-92.

Lutz et al., Creating multiple-crossover DNA libraries independent of sequence identity. Proc Natl Acad Sci U S A. Sep. 25, 2001;98(20):11248-53. Epub Sep. 18, 2001.

Makeyev et al., Evolutionary potential of an RNA virus. J Virol. Feb. 2004;78(4):2114-20.

Malmborg et al., Selective phage infection mediated by epitope expression on F pilus. J Mol Biol. Oct. 31, 1997;273(3):544-51.

Martin et al., Kinetic analysis of T7 RNA polymerase-promoter interactions with small synthetic promoters. Biochemistry. May 19, 1987;26(10):2690-6.

McCafferty et al., Phage antibodies: filamentous phage displaying antibody variable domains. Nature. Dec. 6, 1990;348(6301):552-4.

McConnell et al., Constrained peptide libraries as a tool for finding mimotopes. Gene. Dec. 30, 1994;151(1-2):115-8.

Milligan et al., Oligoribonucleotide synthesis using T7 RNA polymerase and synthetic DNA templates. Nucleic Acids Res. Nov. 11, 1987;15(21):8783-98.

Mills et al., An extracellular Darwinian experiment with a self-duplicating nucleic acid molecule. Proc Natl Acad Sci U S A. Jul. 1967;58(1):217-24.

Nelson et al., Filamentous phage DNA cloning vectors: a noninfective mutant with a nonpolar deletion in gene III. Virology. Jan. 30, 1981;108(2):338-50.

O'Maille et al., Structure-based combinatorial protein engineering (SCOPE). J Mol Biol. Aug. 23, 2002;321(4):677-91.

Opperman et al., A model for a umuDC-dependent prokaryotic DNA damage checkpoint. Proc Natl Acad Sci U S A. Aug. 3, 1999;96(16):9218-23.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.

Riechmann et al., The C-terminal domain of TolA is the coreceptor for filamentous phage infection of *E. coli*. Cell. Jul. 25, 1997;90(2):351-60.

Ringquist et al., Translation initiation in *Escherichia coli*: sequences within the ribosome-binding site. Mol Microbiol. May 1992;6(9):1219-29.

Rosenberg et al., T7 Select® Phage Display System: A Powerful new protein display system based on bacteriophage T7. Innovations. 1996;6:1-6.

Santini et al., Efficient display of an HCV cDNA expression library as C-terminal fusion to the capsid protein D of bacteriophage lambda. J Mol Biol. Sep. 11, 1998;282(1):125-35.

Schultz et al., Oligo-2'-fluoro-2'-deoxynucleotide N3'—>P5' phosphoramidates: synthesis and properties. Nucleic Acids Res. Aug. 1, 1996;24(15):2966-73.

Scott et al., Searching for peptide ligands with an epitope library. Science. Jul. 27, 1990;249(4967):3 86-90.

Sices et al., A genetic screen for the isolation and characterization of site-specific proteases. Proc Natl Acad Sci U S A. Mar. 17, 1998;95(6):2828-33.

Sices et al., Rapid genetic selection of inhibitor-resistant protease mutants: clinically relevant and novel mutants of the HIV protease. AIDS Res Hum Retroviruses. Sep. 1, 2001;17(13):1249-55.

Sieber et al., Libraries of hybrid proteins from distantly related sequences. Nat Biotechnol. May 2001;19(5):456-60.

Smith, Filamentous fusion phage: novel expression vectors that display cloned antigens on the virion surface. Science. Jun. 14, 1985;228(4705):1315-7.

Stemmer, Rapid evolution of a protein in vitro by DNA shuffling. Nature. Aug. 4, 1994;370(6488):389-91.

Sutter et al., Non-replicating vaccinia vector efficiently expresses bacteriophage T7 RNA polymerase. FEBS Lett. Aug. 28, 1995;371(1):9-12.

Tsuji et al., Random multi-recombinant PCR for the construction of combinatorial protein libraries. Nucleic Acids Res. Oct. 15, 2001;29(20):E97.

Tzagoloff et al., The Initial Steps in Infection With Coliphage M13. Virology. Nov. 1964;24:372-80.

(56) References Cited

OTHER PUBLICATIONS

Vidal et al., Yeast forward and reverse 'n'-hybrid systems. Nucleic Acids Res. Feb. 15, 1999;27(4):919-29.
Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.
Voigt et al., Rational evolutionary design: the theory of in vitro protein evolution. Adv Protein Chem. 2000;55:79-160.
Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.
Wang et al., Evolution of new nonantibody proteins via iterative somatic hypermutation. Proc Natl Acad Sci U S A. Nov. 30, 2004;101(48):16745-9. Epub Nov. 19, 2004.
Wang et al., Programming cells by multiplex genome engineering and accelerated evolution. Nature. Aug. 13, 2009;460(7257):894-8. Epub Jul. 26, 2009.
Wharton et al., A new-specificity mutant of 434 repressor that defines an amino acid-base pair contact. Nature. Apr. 30-May 6, 1987;326(6116):888-91.
Wharton et al., Changing the binding specificity of a repressor by redesigning an alpha-helix. Nature. Aug. 15-21, 1985;316(6029):601-5.
Wright et al., Continuous in vitro evolution of catalytic function. Science. Apr. 25, 1997;276(5312):614-7.
Yuan et al., Laboratory-directed protein evolution. Microbiol Mol Biol Rev. Sep. 2005;69(3):373-92.
Zhou et al., Optimization of the Tet-On system for regulated gene expression through viral evolution. Gene Ther. Oct. 2006;13(19):1382-90. Epub May 25, 2006.
Invitation to Pay Additional Fees for PCT/US/2016/043559, mailed Jan. 12, 2017.
International Search Report and Written Opinion for PCT/US2016/027795 mailed Aug. 11, 2016.
Invitation to Pay Additional Fees for PCT/US2016/044546 mailed Oct. 12, 2016.
International Search Report and Written Opinion for PCT/US2016/044546 mailed Dec. 28, 2016.
International Search Report and Written Opinion for PCT/US2016/043513 mailed Nov. 30, 2016.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Badran et al., Development of potent in vivo mutagenesis plasmids with broad mutational spectra. Nat Commun. Oct. 7, 2015;6:8425. doi: 10.1038/ncomms9425.
Birling et al., Site-specific recombinases for manipulation of the mouse genome. Methods Mol Biol. 2009;561:245-63. doi: 10.1007/978-1-60327-019-9_16.
Boch et al., Breaking the code of DNA binding specificity of TAL-type III effectors. Science. Dec. 11, 2009;326(5959):1509-12. doi: 10.1126/science.1178811.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Buchholz et al., Alteration of Cre recombinase site specificity by substrate-linked protein evolution. Nat Biotechnol. Nov. 2001;19(11):1047-52.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015.
Irion et al., Identification and targeting of the ROSA26 locus in human embryonic stem cells. Nat Biotechnol. Dec. 2007;25(12):1477-82. Epub Nov. 25, 2007.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Santoro et al., Directed evolution of the site specificity of Cre recombinase. Proc Natl Acad Sci U S A. Apr. 2, 2002;99(7):4185-90. Epub Mar. 19, 2002.
Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.
Torres et al., Non-integrative lentivirus drives high-frequency cre-mediated cassette exchange in human cells. PLoS One. 2011;6(5):e19794. doi: 10.1371/journal.pone.0019794. Epub May 23, 2011.
Extended European Search Report, dated May 26, 2017, for EP 16203684.

APPARATUS FOR CONTINUOUS DIRECTED EVOLUTION OF PROTEINS AND NUCLEIC ACIDS

CROSS REFERENCES TO RELATED APPLICATIONS

The present application is a continuation of and claims priority under 35 U.S.C. §120 to U.S. application Ser. No. 13/062,098, now U.S. Pat. No. 9,023,594, filed Apr. 4, 2011, which is a national stage filing under 35 U.S.C. §371 of international PCT application, PCT/US2009/056194, filed Sep. 8, 2009, which claims priority under 35 U.S.C. §119(e) to U.S. provisional patent application Ser. No. 61/094,666, filed Sep. 5, 2008, each of which is incorporated herein by reference.

GOVERNMENT SUPPORT

The invention was supported by National Institutes of Health Grant No.: NIH RO1 GM065400 renewal. The government has certain rights in the invention.

FIELD OF THE INVENTION

The present invention concerns methods of diversifying nucleic acids and proteins. Specifically, the present invention discloses continuous methods for evolving nucleic acids and proteins.

BACKGROUND OF THE INVENTION

Proteins and nucleic acids employ only a small fraction of the available functionality. There is considerable current interest in modifying proteins and nucleic acids to diversify their functionality. Molecular evolution efforts include in vitro diversification of a starting molecule into related variants from which desired molecules are chosen. Methods used to generate diversity in nucleic acid and protein libraries include whole genome mutagenesis (Hart et al., Amer. Chem. Soc. (1999), 121:9887-9888), random cassette mutagenesis (Reidhaar-Olson et al., Meth. Enzymol. (1991), 208:564-86), error-prone PCR (Caldwell, et al. (1992), PCR Methods Applic. (1992), 2: 28-33), and DNA shuffling using homologous recombination (Stemmer (1994) Nature (1994), 370:389-391). After diversification, molecules with novel or enhanced properties can be selected.

Methods that enable recombination to take place at defined sites without sequence homology have been described. For example, it is possible to recombine unrelated protein-encoding genes by using synthetic oligonucleotides to encode each desired crossover (O'Maille (2002) J. Mol. Biol. 321:677-91; and Tsuji (2001) Nuc. Acids Res. 29:E97). Although this strategy can result in a high likelihood of preserving function after diversification, many fewer sites of recombination, and therefore, fewer novel structures are accessible than if crossover sites were randomly generated. Alternatively, methods allowing a single nonhomologous crossover of two protein-encoding genes have been developed (Sieber (2001) Nat. Biotechnol. 19:456-60; and Ostermeier (1999) Nat. Biotechnol 17:1205-9), and additional nonhomologous recombination events can be obtained by fragmenting and homologously recombining the resulting genes (Lutz (2001) Proc. Natl. Acad. Sci. USA 98:11248-5317). Despite efforts to enhance the number of crossovers obtained, existing methods for diversifying proteins by nonhomologous recombination have thus far yielded only modest numbers of recombination events (three or fewer per 500 base pair (bp) in protein-encoding sequences, with even fewer crossovers (one to two per 500 bp) among sequences encoding active proteins (Kawarasaki (2003) Nuc. Acids Res. 31:e12618).

While laboratories have explored various aspects of continuous evolution, no generalizable, continuous directed evolution system has been reported. For example, the Joyce laboratory has recently reported continuous evolution of RNA ligase ribozymes. However, their system cannot be generalized to evolve protein functionalities, and is sharply limited in the types of ribozyme activity that can be selected for. (Wright M C, Joyce J F (1997). *Science* 276: 614-617). The Loeb laboratory created an error-prone polymerase I mutant that selectively diversifies sequences downstream of the colE1 plasmid origin and used it to evolve beta lactamase to resist azneotram (Camps M, Naukkarinen J, Johnson B P, Loeb L A (2003). *Proc. Natl. Acad. Sci. USA* 100: 9727-9732). However, reliable continuous mutagenesis was not achieved, selections were performed in slow, discrete rounds, and the entire cell was the object of the selection rather than the construct encoding the resistance gene alone. The Bamford laboratory cloned the beta lactamase gene into the genome of the carrier-state RNA virus phi6 in *P. aeruginosa*. (Makeyev E B, Bamford D H (2004). *J. Virol.* 78: 2114-2120). Error-prone replication of the RNA virus genome and the beta lactamase gene resulted in a library which was selected for cefotaxime resistance over four passages. While mutagenesis was continuous, the passaging and therefore selection was slow and discrete, the library was not transmitted from cell to cell, and the cell was the object of selection. In addition, the Church laboratory has recently (Wang H H et al., (2009). *Nature* 460: 894-898) described a MAGE system, which automates the iterative transformation of bacterial cells with nucleic acids. However, there is no intrinsic means of screening or selecting for a desired function; that is, functional mutants are not selected for without discrete intervention. As such, MAGE represents an important advance over traditional directed evolution techniques, but is not truly continuous and remains considerably slower and more limited in library size than the present invention.

Accordingly, a need exists for a continuous, generalizable, effective method of evolving nucleic acids and proteins.

SUMMARY OF THE INVENTION

In one aspect, the invention discloses methods of generalizable, continuous directed evolution. The invention discloses methods of passing a nucleic acid from cell to cell in a function-dependent manner. Any cell type can be used, so long as the cells are capable of receiving nucleic acids from another cell. Various systems of transferring nucleic acid between cells useful in the present invention include, for example, conjugal transfer (mating) between the first host cell and the second host cell; phage or viral infection, wherein the first host cell is capable of encapsulating the functional nucleic acids and providing entry to the second host cell; and expulsion of the functional nucleic acid from the first cell (e.g., secretion or lysis), wherein the naked nucleic acid strand is taken up by the second host cell. In some embodiments, the system utilizes essential phage genes as reporter genes for library functionalities and subsequent selections.

In one aspect, the invention provides a method of continuous evolution of nucleic acids including introducing at least one functional nucleic acid strand to be evolved into a first host cell; replicating the functional nucleic acid strand within the first host cell; mutating the functional nucleic acid strand; and introducing at least one of the mutated functional nucleic acid strands into a second host cell. The steps of the method can be repeated, resulting in an evolved nucleic acid. The nucleic acid strand can be exogenous or endogenous to the host cells. The host cells can be selected from the group consisting of a prokaryotic cell, a eukaryotic cell, and a bacterial cell.

The host cell can be engineered to screen for a selected function of the expressed nucleic acid strand. Non-limiting examples of selected functions include, for examples, target protein binding, target DNA binding, target RNA binding, transcriptional activation, bond formation catalysis, bond cleavage catalysis, proteolysis, RNA trans-splicing, recombination, site-specific nuclease activity, and intein splicing.

In some embodiments, the step of screening can comprise at least one of abacteriophage display system, an antibiotic resistance and an expression of a reporter gene. In another embodiment, the host cell can further comprises a helper plasmid comprising a phage genome in which one or more of a phage packaging signal and a phage replication signal (a "propagation signal" or "propagation component") is functionally disabled; and an accessory plasmid capable of supplying one or more of the disabled signals in response to the functional expressed nucleic acid strand. In one embodiment, the functional nucleic acid strand can comprise a gene to be evolved and a second gene encoding a propagation component. The propagation component can be required for replication of the functional nucleic acid strand in the first host cell. The propagation component can also be required for introduction of the functional nucleic acid strand into the second host cell.

The phage propagation signal can be functionally disabled through, for example, inactivation of at least one of gene II protein (g2p), gene III protein (g3p), or gene VI protein (g6p). In some embodiments, the helper plasmid and accessory plasmid can be in a single plasmid. Also in some embodiments, the filamentous phage genome is selected from the group consisting of an M13 phage genome, an fd page genome, an fl phage genome, a ZJ/2 phage genome, an Ec9 phage genome, an AE2 phage genome, an HR phage genome, a δA phage genome, and an Ike phage genome.

In some embodiments, the step of introducing the mutated functional nucleic acid strand into a second host cell further comprises culturing the first host cell, wherein the first host cell is capable of packaging phagemid nucleic acid molecules encoded by the functional nucleic acid strand into phage particles. In other embodiments, the step of introducing the mutated functional nucleic acid strand into a second host cell further comprises introducing the filamentous phage particles comprising the packaged phagemid nucleic acid molecules into the second host cell, such that the nucleic acid strand to be evolved is introduced into the second host cell, wherein the second host cell comprises the helper plasmid and the accessory plasmid.

In some embodiments, the step of mutating the functional nucleic acid strand further comprises expressing an evolved protein encoded by the mutated functional nucleic acid strand.

In some embodiments, the step of mutating the functional nucleic acid strand comprising introducing a mutation-inducing agent. The mutation-inducing agent can be selected from the group consisting nucleotide analogues, nucleoside precursors, alkylating agents, cross-linking agents, genotoxins, and radiation. In a preferred embodiment, the mutation-inducing agent is a chemical mutagen. Non-limiting examples of a chemical mutagen useful in the present invention include, for example, 3-Chloro-4-(dichloromethyl)-5-hydroxy-2(5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethyl-thio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9) and t-butyl hydroperoxide (BHP) (CAS no. 75-91-2).

In some embodiments, the host cell can be engineered to inducibly express SOS mutagenizing lesion-bypass proteins. The SOS mutagenizing lesion-bypass proteins can include, for example, polymerase V and activated recA. In other embodiments, the host cell comprises a mutagenic plasmid capable of inducibly expressing an error-prone DNA polymerase subunit.

In some embodiments, the accessory plasmid is capable of inducibly expressing one or more disabled signals from the helper plasmid.

In some embodiments, the method further comprises isolating the mutated nucleic acid strands.

In one embodiment, a continuous evolution system according to the present invention can comprise four biological components: (i) a host cell; (ii) a "helper phagemid", present in the host cells, encoding all phage proteins except a phage replication, packaging or infection component ("the propagation component"); (iii) an "accessory plasmid", also present in the host cells, that expresses a gene for the missing propagation component; and (iv) a "selection phagemid" expressing a member of the library of proteins or nucleic acids being evolved. Following initial infection of a host cell with a selection phagemid, the host cell is subjected to mutagenesis. As a result of mutagenesis, new selection phagemids will evolve. "High-fit" phagemids encode diversified library members as well as expression of the propagation component from the accessory plasmid and can replicate into new phage particles that contain all the necessary components for propagation. The new phage particles can infect new cells, leading to further replication of the fit selection phagemids. In contrast, low-fitness phagemids encode library members incapable of inducing expression of the missing propagation component and are packaged into phage particles lacking this component. These propagation-deficient phage particles are non-infectious, and therefore low-fitness phagemids cannot propagate. Because expression of the propagation component can be linked to a range of protein binding, nucleic acid binding, or reaction catalysis events using many previously developed n-hybrid strategies, this system has the potential to be applicable to a wide variety of protein or nucleic acid activities of interest.

In another aspect, the invention discloses kits and systems of continuous directed evolution system capable of passing a nucleic acid strand from a first cell to a second cell in a function-dependent manner.

DETAILED DESCRIPTION OF THE INVENTION

Figure 1:
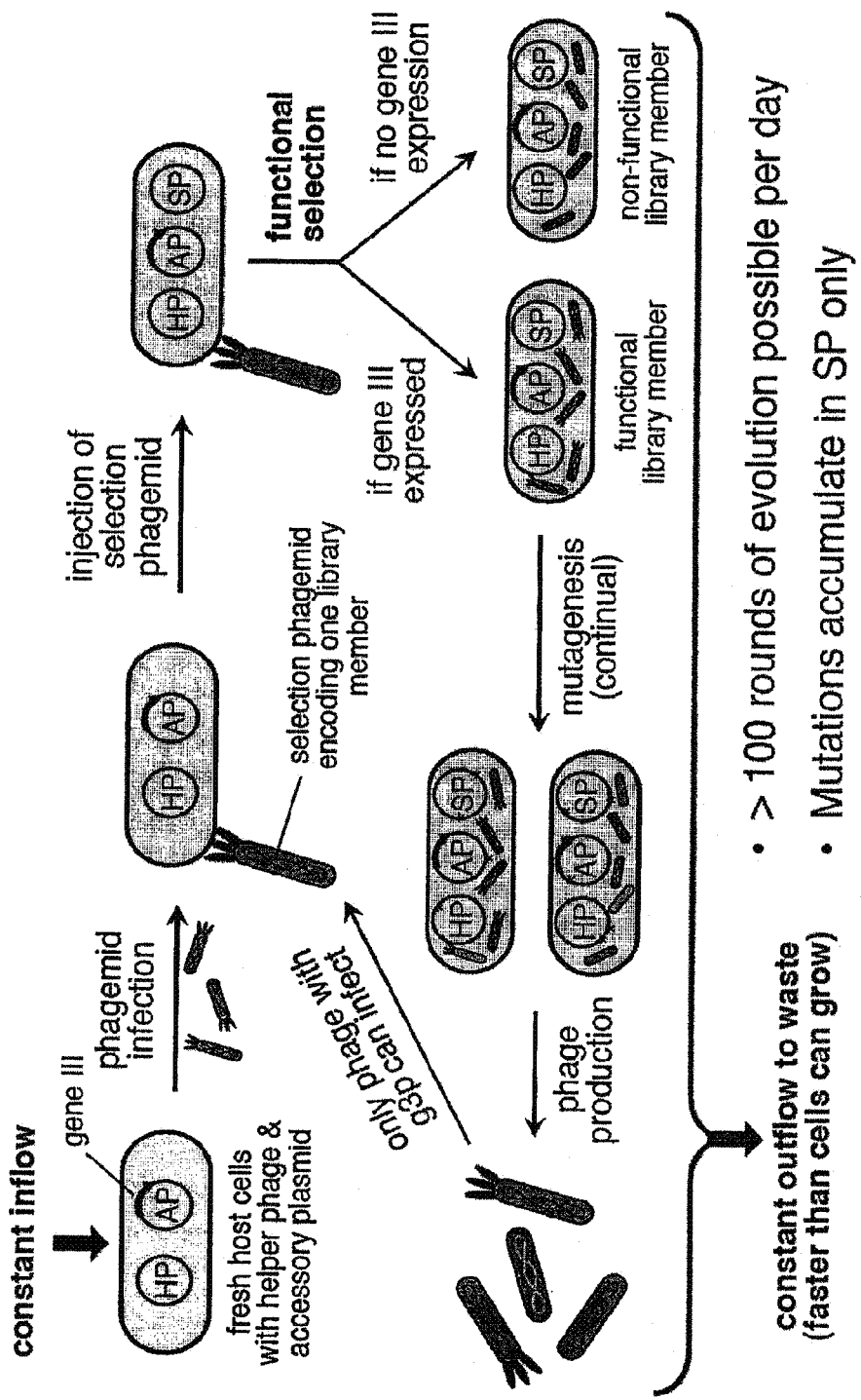
FIG. 1 depicts the selection of phagemids that induce g3p expression and replication of the fit selection phagemids.

The terms used in this invention are, in general, expected to adhere to standard definitions generally accepted by those having ordinary skill in the art of molecular biology. A few exceptions, as listed below, have been further defined within the scope of the present invention.

The term "evolved" refers to a process of change that results in the production of new nucleic acids and polypeptides that retain at least some of the structural features or elements and/or functional activity of the parent nucleic acids or polypeptides from which they have developed. In some instances, the evolved nucleic acids or polypeptides have increased or enhanced activity compared with the parent. In some instances, the evolved nucleic acids or polypeptides have decreased or reduced activity compared with the parent.

The term "non-homologous" refers to two nucleic acid sequences having sufficient number of differences that the two sequences are unable to recombine with each other in a standard host cell, particularly in an *E. coli* cell. The term "in vitro non-homologous" refers to two nucleic acid sequences having sufficient number of differences that the two sequences are unable to recombine using an in vitro recombination method such as the recombination method generally described in Stemmer (Nature (1994), 370:389-391).

The term "shuffled" refers to a molecule having at least one fragment rearranged, reoriented, inserted, or deleted with respect to an appropriate reference polymer, e.g., a parent molecule. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), e.g., in an artificial, and optionally recursive, fashion. In some (but not all) shuffling embodiments, it is desirable to perform multiple rounds of recombination prior to selection to increase the diversity of the pool to be screened. The overall process is optionally repeated recursively. Depending on context, shuffling can refer to an overall process of recombination and selection, or, alternately, can simply refer to the recombinational portions of the overall process.

The terms "nucleic acids," "nucleic acid strand," and "polynucleotide" refer to a polymeric form of nucleotides of any length, either ribonucleotides or deoxyribonucleotides. These terms include a single-, double- or triple-stranded DNA, genomic DNA, cDNA, genomic RNA, mRNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P—NH$_2$) or a mixed phosphoramidate-phosphodiester oligomer (Peyrottes et al. (1996) Nucleic Acids Res. 24: 1841-8; Chaturvedi et al. (1996) Nucleic Acids Res. 24: 2318-23; Schultz et al (1996) Nucleic Acids Res. 24: 2966-73). A phosphorothioate linkage can be used in place of a phosphodiester linkage (Braun et al. (1988) J. Immunol. 141: 2084-9; Latimer et al. (1995) Molec. Immunol. 32: 1057-1064). In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of nucleic acid strands: a gene or gene fragment, exons, introns, genomic RNA, mRNA, tRNA, rRNA, ribozymes, cDNA, recombinant polynucleotides, branched polynucleotides, plasmids, vectors, isolated DNA of any sequence, and isolated RNA of any sequence. A nucleic acid strand may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A nucleic acid strand may be further modified after polymerization, such as by conjugation with a labeling component. Other types of modifications included in this definition are caps, and substitution of one or more of the naturally occurring nucleotides with an analog.

A "mutagenized nucleic acid" is a nucleic acid which has been physically altered as compared to a parental nucleic acid (e.g., such as a naturally occurring nucleic acid), e.g., by modifying, deleting, rearranging, or replacing one or more nucleotide residue in the mutagenized nucleic acid as compared to the parental nucleic acid.

A "transcribed" nucleic acid is a nucleic acid produced by copying a parental nucleic acid, where the parental nucleic acid is a different nucleic acid type than the copied nucleic acid. For example, an RNA copy of a DNA molecule (e.g., as occurs during classical transcription) or a DNA copy of an RNA molecule (e.g., as occurs during classical reverse transcription) can be a "transcribed nucleic acid" as that term is intended herein. Similarly, artificial nucleic acids, including peptide nucleic acids, can be used as either the parental or the copied nucleic acid (and artificial nucleotides can be incorporated into either parental or copied molecules). Copying can be performed, e.g., using appropriate polymerases, or using in vitro artificial chemical synthetic methods, or a combination of synthetic and enzymatic methods.

An "in vitro translation reagent" is a reagent which is necessary or sufficient for in vitro translation, or a reagent which modulates the rate or extent of an in vitro translation reaction, or which alters the parameters under which the reaction is operative. Examples include ribosomes, and reagents which include ribosomes, such as reticulocyte lysates, bacterial cell lysates, cellular fractions thereof, amino acids, t-RNAs, etc.

The terms "propagation component" and "propagation signal" are used interchangeably and refer to one or more proteins or nucleic acids that are required for phage replication, packaging or infection. The propagation component can comprise a phage packaging signal or a phage propagation signal.

The phrase "signal is functionally disabled" refers to a signaling pathway which has been altered so that a specific function is inactive. For example, the phage propagation signal can be disabled through the inactivation of one or more genes in the pathway, or inhibiting the binding of an essential element. "Phage packaging signal" refers to a stretch of residues recognized by the phage packaging proteins. "Phage propagation signal" is intended to include genes and functional RNAs involved in phage propagation. For example, the phage packaging signal can be disabled on the helper plasmid to ensure that only the selection phagemid is packaged and exported. Selection can occur based on the presence of a missing essential gene to phage propagation. Inactivation can result from, for example, truncation, deletion, modification, or through the introduction of one ore more stop codons within an essential gene. In some embodiments, a selectable marker such as an antibiotic resistance marker is included. For example, phage propagation can be disabled through inactivation of one or more of the gene III protein (g3p), gene VI protein (g6p), gene VII protein (g7p), gene VIII protein (g8p), or gene IX protein (g9p) genes. In preferred embodiments, one or more of the gene II protein (g2p), gene III protein (g3p), or gene VI protein (g6p) can be inactivated.

A "functional nucleic acid strand" refers to a nucleic acid strand capable of supplying a selected function. Non-limiting examples of selected functions include target protein binding, target DNA binding, target RNA binding, transcriptional activation, bond formation catalysis, bond cleavage catalysis, proteolysis, RNA trans-splicing, recombination, site-specific nuclease activity, and intein splicing.

A "translation product" is a product (typically a polypeptide) produced as a result of the translation of a nucleic acid. A "transcription product" is a product (e.g., an RNA, optionally including mRNA, or, e.g., a catalytic or biologically active RNA) produced as a result of transcription of a nucleic acid.

The term "random" refers to condition wherein events are determined by a probability distribution. The distribution may include a bias, e.g., dependent on the relative concentrations of starting material. For example, in one embodiment, the parental nucleic acid strands may include a biased amount of one species relative to another. The ligation of a mixture of fragments generated from such a pool of starting material can nevertheless be random.

The term "oligonucleotide," as used herein refers to a nucleic acid polymer of about 5 to 140 nucleotides in length.

The term "protein," as used herein refers to a sequence of amino acids that have a function and/or activity. Examples of activities of proteins include, but are not limited to, enzymatic activity, kinase activity, and binding activity, which can be shown through a variety of spectroscopic, radioactive, or direct binding assays which are known in the art. For example, see Sigma Aldrich for a collection of test kits and assays for biological activity.

The term "binds," and "binding" refer to a physical interaction for which the apparent dissociation constant of two molecules is at least 0.1 mM. Binding affinities can be less than about 10 $\mu$M, 1 $\mu$M, 100 nM, 10 nM, 1 nM, 100 pM, 10 pM, and so forth. The term "ligand" refers to a compound which can be specifically and stably bound by a molecule of interest.

As used herein, "vector (or plasmid)" refers to discrete elements that are used to introduce heterologous DNA into cells for either expression or replication thereof. Selection and use of such vehicles are well known within the skill of the artisan. An expression vector includes vectors capable of expressing DNA's that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "a promoter region or promoter element" refers to a segment of DNA or RNA that controls transcription of the DNA or RNA to which it is operatively linked. The promoter region includes specific sequences that are sufficient for RNA polymerase recognition, binding and transcription initiation. This portion of the promoter region is referred to as the promoter. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in prokaryotes include the bacteriophage T7 and T3 promoters, and the like.

As used herein, "operatively linked or operationally associated" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA. In order to optimize expression and/or in vitro transcription, it may be necessary to remove, add or alter 5' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, e.g., Kozak, J. Biol. Chem., 266: 19867-19870 (1991)) can be inserted immediately 5' of the start codon and may enhance expression. The desirability of (or need for) such modification may be empirically determined.

The term "mutation-inducing agent" can be a chemical mutagen or radiation using, for example, UV, gamma-irradiation, X-rays, and fast neutrons. Chemical mutagens are classifiable by chemical properties, e.g., alkylating agents, cross-linking agents, genotoxins, etc. The following chemical mutagens are useful, as are others not listed here, according to the invention. N-ethyl-N-nitrosourea (ENU), N-methyl-N-nitrosourea (MNU), procarbazine hydrochloride, chlorambucil, cyclophosphamide, methyl methanesulfonate (MMS), ethyl methanesulfonate (EMS), diethyl sulfate, acrylamide monomer, triethylene melamin (TEM), melphalan, nitrogen mustard, vincristine, dimethylnitrosamine, N-methyl-N'-nitro-Nitrosoguani-dine (MNNG), 7,12 dimethylbenz (a) anthracene (DMBA), ethylene oxide, hexamethylphosphoramide, bisulfan. Chemical mutagens useful in the present invention can also include, for example, sodium bisulfite, nitrous acid, hydroxylamine, hydrazine or formic acid. Other agents which are analogues of nucleotide or nucleoside precursors include nitrosoguanidine, 5-bromouracil, 2-aminopurine, 5-formyl uridine, isoguanosine, acridine and of N4-aminocytidine, N1-methyl-N4-aminocytidine, 3,N4-ethenocytidine, 3-methylcytidine, 5-hydroxycytidine, N4-dimethylcytidine, 5-(2-hydroxyethyl)cytidine, 5-chlorocytidine, 5-bromocytidine, N4-methyl-N4-aminocytidine, 5-aminocytidine, 5-nitrosocytidine, 5-(hydroxyalkyl)-cytidine, 5-(thioalkyl)-cytidine and cytidine glycol, 5-hydroxyuridine, 3-hydroxyethyluridine, 3-methyluridine, O2-methyluridine, O2-ethyluridine, 5-aminouridine, O4-methyluridine, O4-ethyluridine, O4-isobutyluridine, O4-alkyluridine, 5-nitrosouridine, 5-(hydroxyalkyl)-uridine, and 5-(thioalkyl)-uridine, 1,N6-ethenoadenosine, 3-methyladenosine, and N6-methyladenosine, 8-hydroxyguanosine, O6-methylguanosine, O6-ethylguanosine, O6-isopropylguanosine, 3,N2-ethenoguanosine, O6-alkylguanosine, 8-oxo-guanosine, 2,N3-ethenoguanosine, and 8-aminoguanosineas well as derivatives/analogues thereof. Examples of suitable nucleoside precursors, and synthesis thereof, are described in further detail in USSN 20030119764. Generally, these agents are added to the replication or transcription reaction thereby mutating the sequence. Intercalating agents such as proflavine, acriflavine, quinacrine and the like can also be used. The use of one or more chemical mutagens will allow for the generation of a wide array of nucleic acid alterations (such as but not limited to expansions or deletions of DNA segments within the context of a gene's coding region, a gene's intronic regions, or 5' or 3' proximal and/or distal regions, point mutations, altered repetitive sequences). In some embodiments, the chemical mutagen can be selected from the group consisting of 3-Chloro-4-(dichloromethyl)-5-hydroxy-2 (5H)-furanone (MX) (CAS no. 77439-76-0), O,O-dimethyl-S-(phthalimidomethyl)phosphorodithioate (phos-met) (CAS no. 732-11-6), formaldehyde (CAS no. 50-00-0), 2-(2-furyl)-3-(5-nitro-2-furyl)acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9) and t-butyl hydroperoxide (BHP) (CAS no. 75-91-2).

The invention is described in more detail in the following subsections:

I. Overview of the System of Continuous Directed Evolution

Directed evolution has led to significant improvements in the desirable properties of proteins and RNA, but traditional methods severely limit the size of the library tested and the number of rounds of selection. In one embodiment, the present invention provides a general system that overcomes these limitations by harnessing the evolutionary potential of the bacteriophage life cycle to enable the continuous diversification and selection of functional proteins and RNA.

The success of in vivo directed evolution is strongly dependent on the library size and the number of rounds of selection performed (Voigt C A, Kauffman S, Wang Z (2000). *Adv Prot Chem* 55: 79-160). Both factors are limited by the transformation step that transfers the library, prepared in vitro, into the cells for selection. The present invention is a system designed to overcome these limitations by performing continuous library diversification and selection in vivo.

In a traditional in vivo directed evolution experiment, the gene to be evolved is diversified by error-prone PCR or DNA shuffling, transformed into bacterial cells, and the most fit variants are identified by a selection or screen. These survivors are isolated, cultured, and the DNA extracted and sequenced to identify the "winning" sequences, which are then subjected to another round of evolution. Each round requires days to weeks, is limited to $\sim 10^{10}$ library members by the transformation step, and requires intensive labor by a person skilled in the art.

The present invention avoids these problems by abandoning the discrete, round-by-round approach in favor of continuously diversifying the gene under selection and continuously selecting for the fittest variants. The library replicates in the manner of a bacteriophage infecting a continuous stream of host bacteria, where the host cells are engineered to allow only functional library members to infect and replicate. As such, the library can evolve as rapidly as the bacteriophage life cycle permits, avoids the size-limiting transformation step entirely, and requires only fresh growth media to continue evolving autonomously.

For example, in one embodiment of the invention, a gene to be evolved can be cloned into a phagemid vector that can be packaged, exported, and infected into host cells, such as a phage, see FIG. 1. Host cells containing all the requisite phage genes are grown at constant growth phase in a turbidostat, see FIG. 2. A continuous flow of host cells are pumped into the lagoon, where they are infected with the phagemid. The phagemid replicates by infecting new cells, while the cells themselves are diluted out faster than they can replicate (Husimi Y (1989). *Adv Biophys* 25: 1-43). Addition of a mutagen-inducing agent or induction of error-prone polymerases selectively mutagenizes the phagemid, the only replicating element in the system. The 10 minute generation time of filamentous phage, high phage densities, and scalable volume enable libraries of up to $10^{11}$ members to undergo >100 rounds of diversification and selection in the course of 24 hours.

The system can evolve any gene whose function can be linked to the production of a phage protein critical for the infection step. Filamentous phage capsids require the presence of phage gene III protein (g3p) to infect host cells, with infectivity increasing more than $10^8$ fold in the presence of g3p. Host cells do not initially express their copy of gene III, so only phagemids capable of inducing g3p production (in a selection-dependent manner tailored to the desired functionality) produce progeny capable of continuing the cycle. In some cases, a recombinase-mediated inversion step or a small molecule-dependent riboswitch may be required to completely prevent gIII expression prior to infection. Library members able to strongly induce g3p production replicate at the expense of those which cannot. In other embodiments, the phage propagation signal can be functionally disabled through inactivation of at least one of gene II protein (g2p), gene III protein (g3p), or gene VI protein (g6p).

One aspect of the invention is demonstrated as a schematic diagram in FIG. 1. One embodiment of the invention can comprise a continuous evolution system with the following components: (i) a host cell; (ii) a "helper phagemid", present in the host cells, encoding all phage proteins except a the propagation component; (iii) an "accessory plasmid", also present in the host cells, that expresses a gene for the missing propagation component, such as gene III protein (g3p); and (iv) a "selection phagemid" expressing a member of the library of proteins or nucleic acids being evolved. The helper phagemid and the accessory phagemid can also be part of a single phagemid.

In a further aspect of the invention, the host cell is subjected to mutagenesis. Mutagenesis can be induced in the host cells by methods known to those skilled in the art, such as, but not limited to, chemical mutagens, mutagenic enzymes (error prone polymerases). High mutagenesis rates are possible since because the only replicating element in the system is the phagemid carrying the gene of interest. These levels can be attained, for example, through high doses of chemical mutagens delivered continuously into the lagoon or culture media. Base analog mutagens take effect immediately, but alkylating mutagens require the induction of the SOS response in *E. coli* to cause mutagenesis. As full induction of the SOS response, which includes production and activation of the error-prone lesion bypass polymerase V, only occurs 20-40 minutes after the initial DNA damage (Opperman T, Murli S, Smith B T, Walker G C (1999). *Proc. Natl. Acad. Sci. USA* 96: 9218-9223), the present invention utilizes a mutagenesis plasmid that immediately expresses the relevant elements (umuD', umuC, recA730) upon exposure to arabinose. Additionally, one embodiment of the present invention has the option of inducing a dominant negative proofreading subunit of the main replicative polymerase, such as dnaQ926, which dramatically increases the natural mutagenesis rate during phagemid replication (Fijalkowska I, Schaaper R (1996). *Proc. Natl. Acad. Sci. USA* 93: 2856-2861). As a result of the mutagenesis, new selection phagemids can evolve.

A major problem with traditional directed evolution, whether in vitro or in vivo, is that libraries that do not contain any functional variants will be entirely lost, and the effort wasted—even if functionality lies only a couple of mutations away. The present invention overcomes this problem by allowing "switchable" genetic drift. This can be achieved by, for example, providing "free" propagation components to all library members, such as by inducible expression from an anhydrotetracycline-regulated titratable promoter, enabling all variants to infect host cells. By providing enough "free" propagation components, but less than the optimal level, any functional variants that arise will produce slightly more of the missing propagation components, produce more infectious progeny, and take over the population.

Another aspect of the invention can comprise screening for a selected function of the evolved library of proteins or nucleic acids. After evolution of the library of proteins or nucleic acids, a selection display system can be used in conjunction with a library according to the invention. Examples of selection display systems are known by those skilled in the art and can be, but are not limited to, bacteriophage, selective growth media (antibiotic resistence), expression of a reporter gene or protein fluorescence (i.e. fluorescent protein expression and LacZ/X-gal blue/white color change) and utilizing varying strengths of ribosome binding sites (RBS) to influence translation. Preferred selection systems of the invention are the bacteriophage systems. Selection protocols for isolating desired members of large libraries are known in the art, as typified by phage display techniques. An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

In one embodiment, the bacteriophage system can be used for selection. "High-fit" phagemids can encode the diversified library members as well as expressing the missing propagation component from the accessory plasmid and can replicate into new phage particles that contain all the necessary components for propagation. The new phage particles can infect new cells, leading to further replication of the fit selection phagemids. In contrast, low-fitness phagemids encode library members incapable of inducing expression of the missing propagation component and are packaged into phage particles lacking this component. These propagation-deficient phage particles are non-infectious, and therefore low-fitness phagemids cannot propagate. Because expression of the library of proteins or nucleic acids being evolved can be linked to a range of protein binding, nucleic acid binding, or reaction catalysis events using many previously developed n-hybrid strategies, this system has the potential to be applicable to a wide variety of protein or nucleic acid activities of interest.

In another embodiment of the invention, individual clones can be isolated. For example, bacteriophage particles present in the cellstat at the end of the experiment can infect host cells, alternatively their DNA is transformed into host cells and the cells can be grown on media-containing plates in the presence of an appropriate selection marker, e.g., antibiotic. Each colony represents an individual DNA sequence encoding the evolved library of proteins or nucleic acids. The evolved DNA sequences can be isolated from the host cell colony by standard means. The evolved DNA sequences can then be cloned into an eukaryotic or prokaryotic expression vector for the expression of soluble polypeptide.

II. Overview of Phage Display

Phage display utilizes bacteriophages to display varied polypeptides. The display protein can be linked to a bacteriophage coat protein with covalent, non-covalent, and non-peptide bonds. See, e.g., U.S. Pat. No. 5,223,409, Crameri et al. (1993) Gene 137:69 and WO 01/05950. The linkage can result from translation of a nucleic acid encoding the varied component fused to the coat protein. The linkage can include a flexible peptide linker, a protease site, or an amino acid incorporated as a result of suppression of a stop codon.

Phage display is described, for example, in Ladner et al., U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; WO 90/02809; de Haard et al. (1999) J. Biol. Chem 274: 18218-30; Hoogenboom et al (1998) Immunotechnology 4:1-20; Hoogenboom et al. (2000) Immunol Today 2:371-8; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Rebar et al. (1996) Methods Enzymol. 267:129-49; Hoogenboom et al. (1991) Nuc Acid Res 19:4133-4137; and Barbas et al. (1991) PNAS 88:7978-7982.

Phage display systems have been developed for Ff filamentous phage (phage fl, fd, and M13) as well as other bacteriophage (e.g. T7 bacteriophage and lambdoid phages; see, e.g., Santini (1998) J. Mol. Biol. 282:125-135; Rosenberg et al. (1996) Innovations 6:1-6; Houshm et al. (1999) Anal Biochem 268:363-370).

Phage display technology, i.e., the use of filamentous phage to display recombinant proteins and peptides, is well known and can be used for selecting proteins and peptides with desired functions or improved characteristics from complex libraries. Phage display is widely used for the isolation of human antibodies through clonal selection of antibody fragments in prokaryotic host systems. Filamentous phage from the Ff group, including M13, fl and fd phage, are commonly used. Vectors capable of directing the generation of recombinant phage and phagemid expressing fusions of viral coat proteins with proteins of interest in *E. coli* have been developed and are widely available. There are two broad categories of vectors used for phage display: phage and phagemid.

When proteins are displayed on phage, the gene encoding the recombinant display protein is included in the phage genome. As a result, phage particles display the recombinant protein and contain the recombinant phage genome. In the case of phagemid, the recombinant protein is encoded as a fusion with a gene, such as g3p, on a plasmid (phagemid) which also contains a gene required by the phage for replication, packaging and/or infection. Bacteria carrying such phagemids make large amounts of the recombinant display protein, but are unable to make phage unless the bacteria carrying the phagemid also contain helper phage, which supply all the other proteins required to make functional phage.

Helper phages can be normal Ff phages with a number of modifications: their packaging signal can be severely disabled, they can contain an additional origin of replication, and they can carry antibiotic resistance genes. A disabled packaging signal does not prevent the helper phage from making phage particles when alone in a bacterium, but in the presence of a phagemid, which has an optimal packaging signal, the phagemid can be packaged in preference to the helper phage. As a result, phagemid preparations can be both phenotypically and genotypically heterogeneous. Accordingly, the displayed protein can be either wild type (derived from the helper phage) or recombinant (derived from the phagemid), and the packaged genome can be either phage or phagemid.

Nucleic acids suitable for phage display, e.g., phage vectors, have been described. See, e.g., Armstrong et al. (1996) Academic Press, Kay et al., Ed. pp. 35-53; Corey et al. (1993) Gene 128(1):129-34; Cwirla et al. (1990) Proc Natl Acad Sci USA 87(16):6378-82; Fowlkes et al. (1992) Biotechniques 13(3):422-8; Hoogenboom et al. (1991) Nucleic Acids Res 19(15):4133-7; McCafferty et al. (1990) Nature 348(6301):552-4; McConnell et al. (1994) Gene 151(1-2):115-8; Scott and Smith (1990) Science 249(4967): 386-90.

Phagemids.

An alternative configuration of phage display uses a phagemid vector. In a phagemid system, the nucleic acid encoding the display protein is provided on a plasmid, typically of length less than 6000 nucleotides. The plasmid includes a phage origin of replication so that the plasmid is incorporated into bacteriophage particles when bacterial cells bearing the plasmid are infected with helper phage, e.g. M13K01. Phagemids, however, lack a sufficient set of phage genes in order to produce stable phage particles. These phage genes can be provided by a helper phage. Typically, the helper phage provides an intact copy of gene III and other phage genes required for phage replication and assembly. Because the helper phage has a defective origin, the helper phage genome is not efficiently incorporated into phage particles relative to the plasmid that has a wild type origin. See, e.g., U.S. Pat. No. 5,821,047. The phagemid genome can contain a selectable marker gene, e.g. $Amp^R$ or $Kan^R$ for the selection of cells that are infected by a member of the library.

Phage Vectors.

Another configuration of phage display uses vectors that include a set of phage genes sufficient to produce an infectious phage particle when expressed, a phage packaging signal, and an autonomous replication sequence. For example, the vector can be a phage genome that has been modified to include a sequence encoding the display protein. Phage display vectors can further include a site into which a foreign nucleic acid sequence can be inserted, such as a multiple cloning site containing restriction enzyme digestion sites. Foreign nucleic acid sequences, e.g., that encode display proteins in phage vectors, can be linked to a ribosomal binding site, a signal sequence (e.g., a M13 signal sequence), and a transcriptional terminator sequence.

Phage display systems typically utilize Ff filamentous phage. In implementations using filamentous phage, for example, the display protein is physically attached to a phage coat protein anchor domain. Co-expression of the display protein with another polypeptide having the same anchor domain, e.g., an endogenous copy of the coat protein, will result in competition for expression on the surface of the particle.

Phage coat proteins that can be used for protein display include (i) minor coat proteins of filamentous phage, such as gene III protein, and (ii) major coat proteins of filamentous phage such as gene VIII protein. Fusions to other phage coat proteins such as gene VI protein, gene VII protein, or gene IX protein can also be used (see, e.g., WO 00/71694).

Portions (e.g., domains or fragments) of these proteins may also be used. Useful portions include domains that are stably incorporated into the phage particle, e.g., so that the fusion protein remains in the particle throughout a selection procedure. In one embodiment, the anchor domain or "stump" domain of gene III protein can be used (see, e.g., U.S. Pat. No. 5,658,727 for a description of an exemplary gene III protein stump domain). As used herein, an "anchor domain" refers to a domain that is incorporated into a genetic package (e.g., a phage). A typical phage anchor domain is incorporated into the phage coat or capsid.

In another embodiment, the gene VIII protein can be used. See, e.g., U.S. Pat. No. 5,223,409. The mature, full-length gene VIII protein can be linked to the display protein.

The phage display systems can also use protein fusions to physically attach the heterologous amino acid sequence to a phage coat protein or anchor domain. For example, the phage can include a gene that encodes a signal sequence, the heterologous amino acid sequence, and the anchor domain, e.g., a gene III protein anchor domain.

It is also possible to use other systems to screen for evolved nucleic acid strands. Examples of selection display systems are known by those skilled in the art and can be, but are not limited to, bacteriophage, selective growth media (antibiotic resistence), expression of a reporter gene or protein fluorescence (i.e. fluorescent protein expression and LacZ/X-gal blue/white color change) and utilizing varying strengths of ribosome binding sites (RBS) to influence translation.

Various systems of transferring nucleic acid between cells useful in the present invention include, for example, conjugal transfer (mating) between the first host cell and the second host cell; phage or viral infection, wherein the first host cell is capable of encapsulating the functional nucleic acids and providing entry to the second host cell; and expulsion of the functional nucleic acid from the first cell, wherein the naked nucleic acid strand is taken up by the second host cell. In some embodiments, the system utilizes essential phage genes as reporter genes for library functionalities and subsequent selections.

III. Constraints of Stepwise Directed Evolution

Directed evolution as commonly practiced in cells involves a stepwise process of (i) diversifying a gene of interest into a library of sequence variants; (ii) subcloning the resulting gene library into a vector suitable for in vivo expression; (iii) transforming a population of cells with the vector library; (iv) subjecting the resulting cells to screening or selection; (vi) harvesting surviving cells and extracting their vectors; and (vii) subjecting these surviving genes to a new cycle of directed evolution starting with step (i). While this format for directed evolution has supported many successful applications, its stepwise nature imposes several fundamental constraints.

Some of these constraints can be best visualized by considering a theoretical model known as a "fitness landscape". The fitness of a given protein or nucleic acid is represented by its height in this landscape, with similar sequences located near one another. Closely related sequences of high fitness are depicted as mountain ranges, while low fitness sequences are valleys. The objective of a directed evolution experiment is to discover the highest peak in the fitness landscape by successively diversifying points on the landscape into clusters and eliminating those sequences below a threshold altitude through selection. Survival of a library member represents a step taken on the fitness landscape, ideally resulting in an increase in altitude. The chance of discovering the highest peak in the fitness landscape is maximized when the largest possible library is explored in each round and as many steps as possible are taken on a path toward the fitness summit.

Several factors constrain the amount of sequence space (library size) that can be explored in each round of conventional stepwise directed evolution. Because conventional in vivo selections use alternating cycles of in vitro diversification and in vivo selection connected through the transformation of DNA into cells, library size is limited by transformation efficiency. As a result, in vivo libraries rarely exceed $10^9$-$10^{10}$ sequences. While in vitro libraries of up to $10^{15}$ different species have been reported, the creation of high-complexity ($>10^{10}$ variants) protein libraries in vitro has thus far been limited to peptides of less than 100 amino acids. In addition, in vitro selections are limited predominantly to selections for binding or covalent attachment/detachment and typically do not enable selections for multiple turnover catalysis, while the range of activities that can be selected in living cells can be significantly broader.

Traditional directed evolution methods are also limited in the number of rounds of selection that can be executed in a reasonable set of experiments. The growth, extraction, characterization, cloning, and mutagenesis of genes encoding surviving library members during one round of evolution collectively require significant effort (typically days to weeks). Furthermore, sources of contamination that can ruin directed evolution experiments frequently enter evolving gene pools during these manipulations. The number of rounds over which conventional directed evolution can be performed effectively is often limited by the proliferation of contaminating DNA. These considerations limit the number of evolutionary steps that can be taken over the course of a stepwise in vivo directed evolution endeavor.

In addition to suffering constraints on library size and number of evolutionary steps that can be taken, conventional directed evolution approaches are easily trapped at suboptimal sequences. When evolving populations arrive at a fitness peak that is a local, rather than global, maximum, departure from the local peak toward the global maximum can be very difficult. This problem can be solved by performing rounds of evolution under conditions that require only modest fitness, thereby encouraging broad horizontal migration across the fitness landscape. However, the distance that can be traversed during migration is once again limited by the number of different sequences that can be accessed in each library, and by the time and contamination risk associated with each round of evolution.

IV. Developing a Broadly Applicable System Enabling the Continuous Directed Evolution of Proteins and Nucleic Acids In Vivo In principle the above challenges facing stepwise directed evolution can be addressed by performing the mutation, selection, and amplification of evolving molecules in a continuous, self-sustaining manner. Implementing a continuous evolution system in vivo that can be applied to a wide range of functions mediated by proteins or nucleic acids requires that the diversification of genes of interest take place within cells, and that sequences of higher fitness be preferentially replicated and transmitted to the next generation of cells. Many of the above challenges facing the development of a truly continuous directed evolution system can be addressed by exploiting key features of the viral life cycle. The in vivo directed evolution system of the present invention uses cells to perform the selection, maintenance, and propagation of evolving genes. In one aspect of the invention, the bacteriophage life cycle was used as a framework for truly continuous directed evolution. This system enables directed evolution to solve a wide range of binding and catalysis problems that are not accessible using current methods.

The Examples demonstrate the ability of the cellstat system to enable continuous diversification, selection, and amplification mediated by gene III expression. The key properties of this continuous evolution system were analyzed and the system was tested in an initial evolutionary task. Specifically, the exemplary system was used to (i) correlate the diversification rate in the cellstat with the concentration of chemical mutagen; (ii) develop mechanisms by which the stringency of continuous evolution selections can be modulated; and (iii) validate the complete system by evolving a recombinase enzyme in E. coli.

The continuous evolution system of the present invention can sample a library of about $10^{12}$ sequences at any given moment, representing at least a 100-fold increase over the maximum size of in vivo libraries created by standard methods. In addition, a conservative estimate of about 15 minutes needed to synthesize, export, infect, and replicate evolving genes implies that a viral continuous evolution system will execute the diversification, selection, and amplification steps equivalent to ~100 rounds of conventional directed evolution per day. Such significant increases in evolutionary efficiency enables very rare solutions to difficult problems to be accessed in a time scale of days.

V. Modulating Mutagenesis and Selection Stringency of Continuous Evolution

Control over the mutagenesis rate is crucial to successful directed evolution. A high initial mutation rate enhances sequence exploration by increasing the distance in sequence space traversed in each round. However, high mutation rates can also cause a population to fall off steep and narrow fitness peaks. Therefore, it can be advantageous to diversify at a high rate early in the selection and decrease mutagenesis later, or to punctuate longer periods of modest mutagenesis with brief periods of intense mutagenesis. Example 1 demonstrates the ability of the cellstat system to support continuous mutagenesis mediated by methyl methane sulfonate (MMS). The continuous flow of host cells and chemical mutagen in and out of the cellstat system makes possible the real-time adjustment of mutagenesis rates. The relationship between chemical mutagen concentration and diversification rate by sequencing DNA present in the selection phagemid that is not under selection (such as the chloramphenicol acetyltransferase gene) at various mutagen concentrations and timepoints can be explored. The resulting calibration curve relating mutation rate per hour to MMS concentration can be used to set mutagenesis rates in subsequent experiments.

Implementation of the continuous evolution system described in the present invention is based on linking the function to be evolved to the expression of a propagation signal or component, such as M13 g3p. Because g3p is required to produce infectious phage/phagemids, increased function leads to improved transfer from one cell to another, continuously selecting for greater and greater function up to a theoretical maximum beyond which additional g3p does not increase infection. However, expression of g3p also results in membrane perturbations causing retraction of the F pilus and subsequent resistance to infection. Consequently, leaky expression of g3p prior to infection with the phage or phagemid carrying the nucleic acid to be evolved prevents propagation. The amount of g3p required for significant transfer is far in excess of the amount causing pilus retraction. This problem can be overcome by including a gene encoding a recombinase enzyme on the phage or phagemid, and inverting the g3p expression cassette on the accessory. Recombinase expression after infection inverts the cassette and permits g3p expression, providing an absolute off-to-on switch for g3p transcription. Alternatively, a small molecule-dependent riboswitch can be attached in front of the g3p sequence, preventing translation in the absence of the small molecule. Addition of the small molecule to the cellstat prevents premature g3p expression prior to arrival in the cellstat and infection with a phage/phagemid. Both methods dramatically reduce the level of g3p produced.

Because a large quantity of g3p is required for significant infectious phage production, very strong promoters are needed. In one embodiment, T7 RNA polymerase may be used to produce sufficient protein. A recombinase-mediated inversion step catalyzed by a recombinase encoded on the phage or phagemid can provide a source of g3p sufficient for phage/phagemid propagation, but little enough such that functional phagemids can benefit by producing more. As an alternative to the recombinase option, the psp (phage shock) promoter, which activates upon phage infection, can be used if the gene to be evolved is carried along with the entire phage genome.

Figure 3:
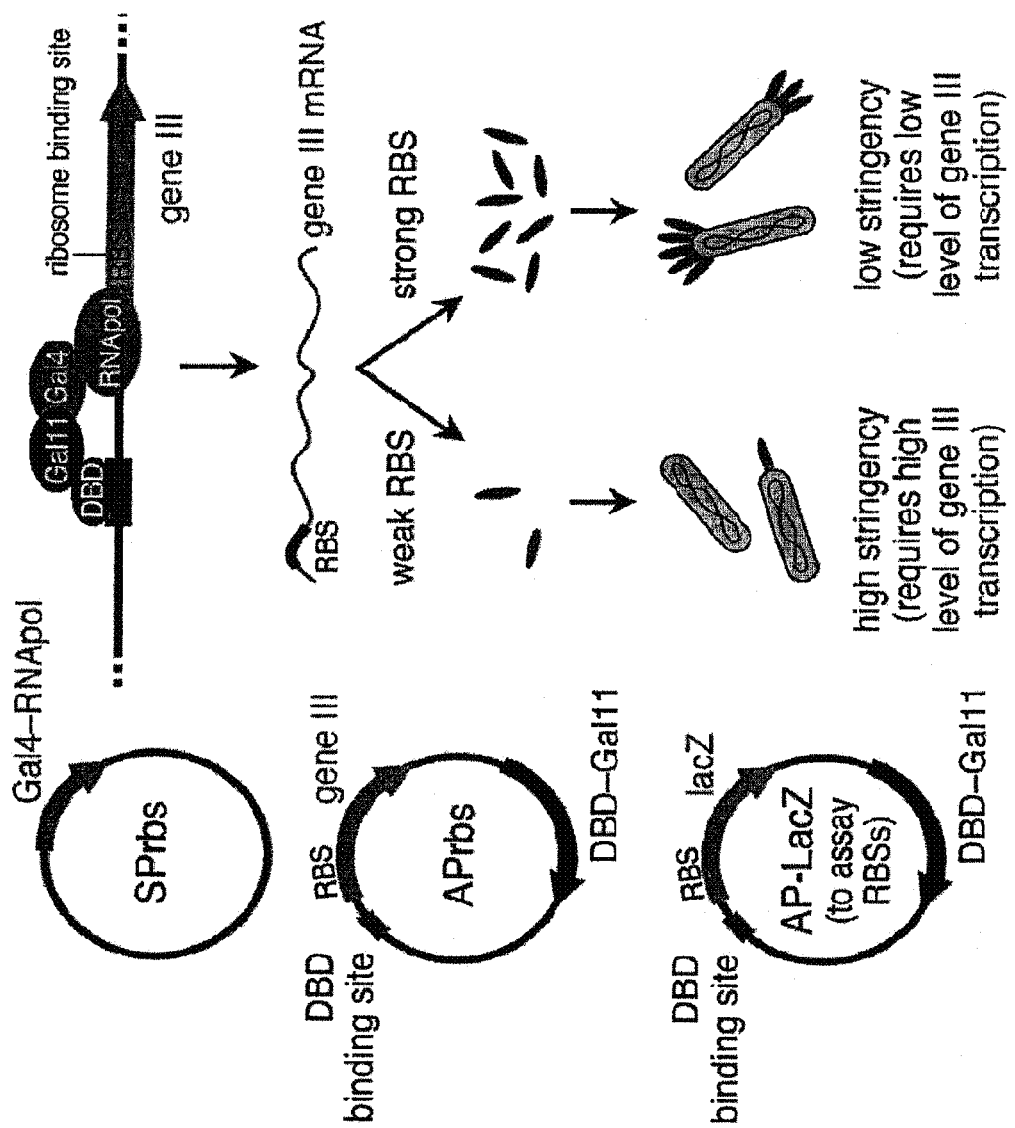
FIG. 3 depicts selection stringency in the continuous evolution system.

In addition to modulating the nature of diversification in the continuous evolution system, a means of controlling selection stringency has been developed. As described above, avoiding local fitness peak traps by promoting the horizontal drift of evolving sequences requires careful control over selection stringency. In the described system, fitness is ultimately determined by the ability to produce sufficient propagation components to render all progeny phage infectious. Because propagation component production may require translation, the strength of the ribosome binding site (RBS) present in the host cell-provided accessory plasmid can also be used to control selection stringency (FIG. 3). A weak RBS sequence results in a high stringency selection because high levels of transcription are required to compensate for low rates of translation. Weak RBS sequences should therefore result in library members with higher average fitness after continuous evolution. Conversely, RBS sequences that are highly effective at initiating translation represent low stringency selection and therefore should result in lower average fitness values after evolution.

RBS sequences can be identified, chosen from a known list of RBS variants with different translational efficiencies, that result in different selection stringencies. These candidate RBS sequences can be placed upstream of the gene for the propagation component, such as g3p in the accessory plasmid, APrbs, which expresses yeast Gal11 fused to a DNA-binding domain (DBD) whose target sequence is located upstream of the gene III promoter. The selection phagemid, such as SPrbs that expresses a yeast Gal4 subunit, can be fused to an subunit of RNA polymerase (RNApol), such as the alpha subunit. An example is the well-characterized interaction between the Gal4 and Gal11 proteins recruits RNApol to the otherwise weak gene III promoter and drives transcription of gene III. During continuous evolution, the selection phagemid, such as Gal4-RNAPol fusion encoded by SPrbs, can be subjected to mutagenesis and selection. Following continuous evolution, the variants from the system can be harvested and their encoded mutants can be assayed, such as by using a reporter construct (AP-LacZ) identical to APrbs but containing lacZ instead of gene III (FIG. 3). In such an example, standard quantitative β-galactosidase assays can be used to determine the average levels of transcriptional activation achieved by Gal4-RNAPol variants evolved using different RBS sequences. These levels represent (by definition) the selection stringency imparted by each RBS. RBS sequences with translation initiation activities outside of the dynamic range that influences selection phagemid fitness level will be disregarded, while RBS sequences that influence the evolutionary outcome will be ranked based on the selections stringencies they impart.

The continuous directed evolution system of the present invention can also be used to characterize the ways in which chemical mutagen concentrations determine diversification rate and accessory plasmid RBS sequence determines selection stringency.

VI. Engineered Zinc-Finger DNA-Binding Domains

A. Overview

The ability to target a recombinase, nuclease, or transcriptional regulator to virtually any gene of interest using a genetically encoded protein domain would significantly advance genomics, genome engineering, and gene therapy research. Prior to this invention, this capability remained an unrealized dream. A single zinc finger domain recognizes three base pairs of DNA. An oligomer of six modules can recognize an 18-nucleotide sequence—a sequence long enough to represent a unique site in the human genome—with potent binding affinity (Kd=~1 nM or better).

A number of challenges must be overcome for artificial zinc-finger domains to represent a general solution to DNA targeting. Modular zinc finger domains capable of binding to 17 of the 64 possible DNA nucleotide triplets have not yet been reported. Moreover, simple assembly of a zinc finger oligomer by fusing modules known to recognize each component triplet will produce a functional binding domain, but due to the imperfect modularity of zinc fingers, the oligomer will not necessarily bind with the target sequence significantly more potently than any other non-target sequence. Stepwise directed evolution methods using phage display or bacterial two-hybrid systems have been used to optimize oligomeric zinc fingers for high-affinity binding. Evolutionary approaches are especially important when creating six-module zinc-finger oligomers, as simple fusion of six modules results in poor binding due to each module extending slightly beyond the geometric parameters of three DNA base pairs. The development of an efficient and accessible method of generating zinc-finger domains with high affinity and high specificity for any desired DNA sequence therefore remains an outstanding challenge.

Once an appropriate zinc finger has been generated, it must be linked to an additional protein domain that can impart the function of interest such as transcriptional regulation, endonuclease activity, or recombinase activity. To generate effective sequence-specific enzymes using this approach requires additional screening or selection to optimize the ways in which the zinc-finger domain and catalytic domains interact, as a simple linkage is not always sufficient. The increased difficulty of generating such hybrid enzymes represents a major barrier to several promising gene therapeutic approaches.

The strengths of the continuous directed evolution approach of the present invention addresses the above challenges facing the generation of zinc-finger DNA-binding domains and zinc-finger targeted recombinases by (i) dramatically augmenting the efficiency of directed evolution, and (ii) enabling evolutionary pressure to be applied simultaneously toward binding and catalysis at target sequences as well as against binding and catalysis at non-target sequences.

B. Tn3-Family Serine Recombinase Enzymes

Not all recombinase enzymes are suitable for targeting by fusion with a zinc-finger domain. For example, the tyrosine recombinases Cre, Flp, and λ integrase, as well as ΦC31 and the larger serine integrases have integrated catalytic and DNA-binding domains. As a result, DNA specificity for these recombinases cannot be changed by the modular replacement of the DNA-binding domain with a zinc finger domain. However, the specificity of the Tn3 family of serine recombinases can be determined by a DNA binding domain attached to a separate catalytic domain through a flexible linker. This arrangement makes Tn3 recombinases ideal for retargeting by replacement of the DNA-binding domain. A close relative of the Tn3 recombinase, γδ, is active in mammalian cells, suggesting that this family may be useful for targeted gene therapy in humans. Zif268-Tn3 has been reported as a zinc-finger-targeted recombinase enzyme, in addition Gordley et al. (Gordley R M et al. (2007). J. Mol. Biol. 367:802-813) described directed evolution of $Rec_{zf}$.

The speed and power of continuous directed evolution can be used to enable zinc finger recombinases (and perhaps other hybrid zinc-finger-targeted enzymes) to evolve activity for virtually any desired DNA sequence on a timescale of days.

Figure 4:
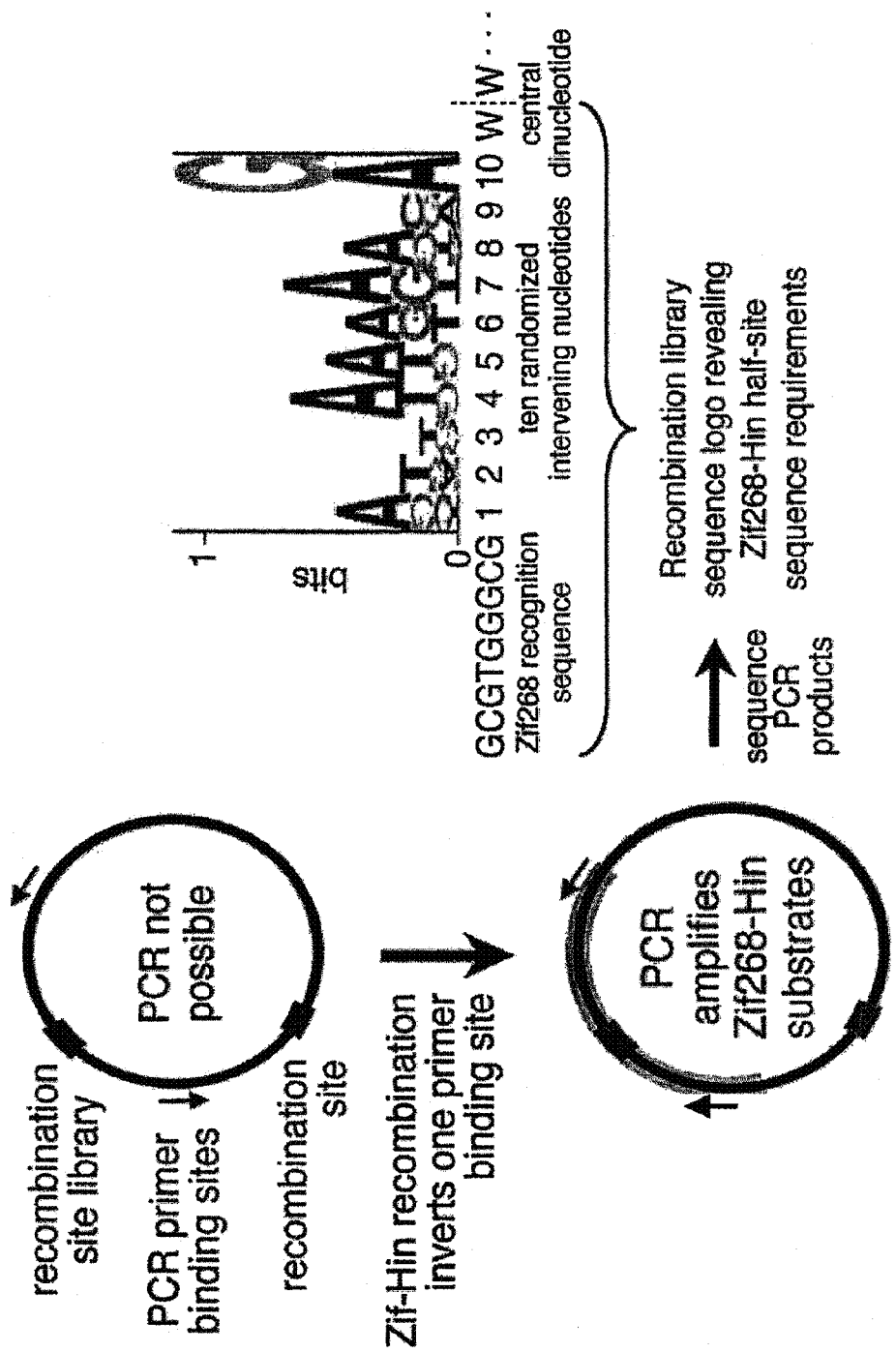
FIG. 4 depicts PCR-based selection of Zif268-Hin recombinase sites.

C. Applying the Continuous Directed Evolution System to Evolve Zinc-Finger DNA-Binding Domains and Recombinase Enzymes that can Specifically Target Virtually any Desired DNA Sequence Hyperactive Hin recombinase (H107Y) can also be suitable for targeting to DNA sequences using zinc-finger-mediated DNA binding (FIG. 4). Hin recombinase can be efficiently retargeted to sites containing zinc-finger recognition sequences and has no sequence requirements beyond the preference for a purine immediately preceding the central dinucleotide undergoing cleavage during recombination. The continuous evolution system of the present invention can be used to rapidly generate both zinc-finger-DNA binding domains and zinc-finger-targeted recombinase enzymes that are capable of binding or catalyzing recombination at any DNA sequence containing a RWWY tetranucleotide (R=A or G; W=A or T; Y=C or T), a motif that occurs approximately every 16 base pairs.

D. Continuous Evolution and Characterization of Zinc-Finger Domains and Zinc-Finger-Targeted Recombinase Enzymes Despite remarkable progress in engineering different zinc-finger domains that can each bind to a different DNA triplet, no zinc-finger motifs can currently target CTC or any of the TNN triplets. This limitation prevents targeting to many potential sequences of interest. Even if this problem were surmounted, the specificity and efficiency of concatenated zinc-finger oligomers remain modest in many cases. The continuous evolution system of the present invention can be applied to rapidly generate highly specific and efficient zinc-finger domains and zinc-finger-targeted Hin recombinases.

Figure 5:
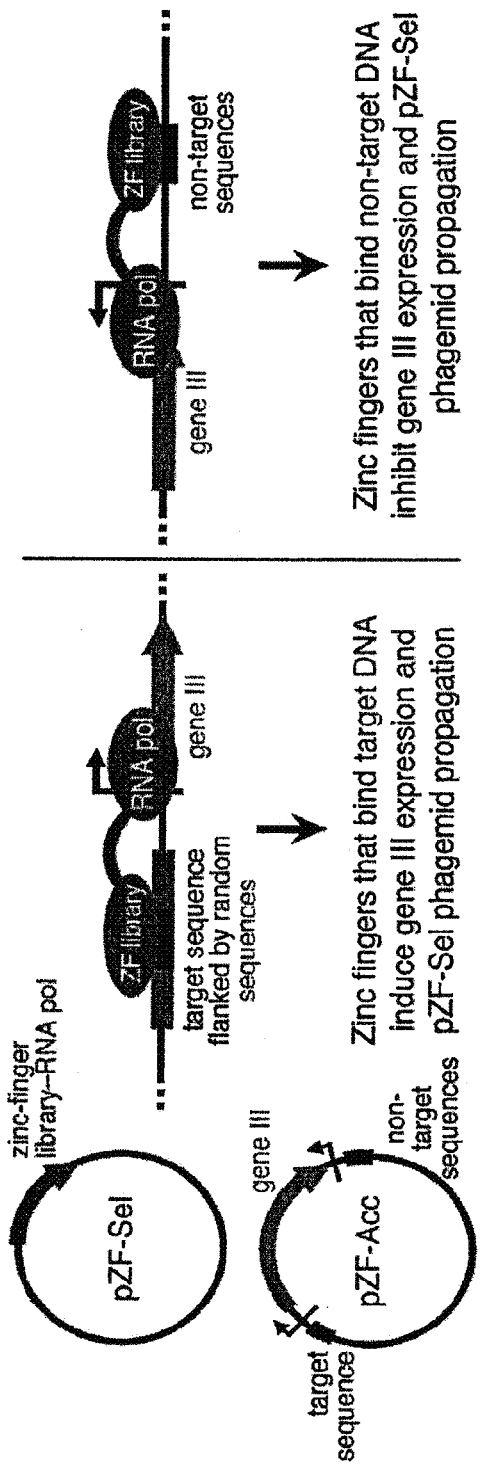
FIG. 5 illustrates the use of pZF-Sel, selection phagemid, and pZF-Acc, accessory phagemid, to evolve zinc-finger binding domains.

To evolve zinc-finger binding domains with virtually any desired DNA sequence specificity, a selection phagemid can be used, such as pZF-Sel that expresses a three zinc-finger library as a fusion with the alpha subunit of RNA polymerase shown in FIG. 5. An example of an accessory plasmid that will accompany pZF-Sel is pZF-Acc (FIG. 5), which contains the desired nine-base zinc-finger target site near the promoter region of gene III. A library of random nucleotides can surround the target site in pZF-Acc. Cells harboring pZF-Acc and pZF-Sel can express g3p if the zinc-finger library member can bind to the target sequence. The random nucleotides surrounding the target site in pZF-Acc disfavor the survival of zinc fingers that activate gene III expression by binding sequences near the target site, rather than the target itself (FIG. 5). The spacing between the zinc-finger binding site and the start of gene III is crucial to activate one-hybrid expression, and therefore zinc-finger binding at more distal sites will not lead to pZF-Sel survival. To exert evolutionary pressure against the binding of DNA other than the target sequence, nontarget sequences can be placed after gene III and near a weak promoter oriented in the gene III antisense direction (FIG. 5). Zinc-finger domains that bind to these non-target sites will induce transcription in the antisense direction of gene III, decreasing gene III expression and inhibiting propagation of selection phagemids encoding zinc fingers with poor specificity. The strength of the two oppositely oriented promoters can be varied to modulate the evolutionary pressure balance of target affinity versus specificity.

Figure 6:
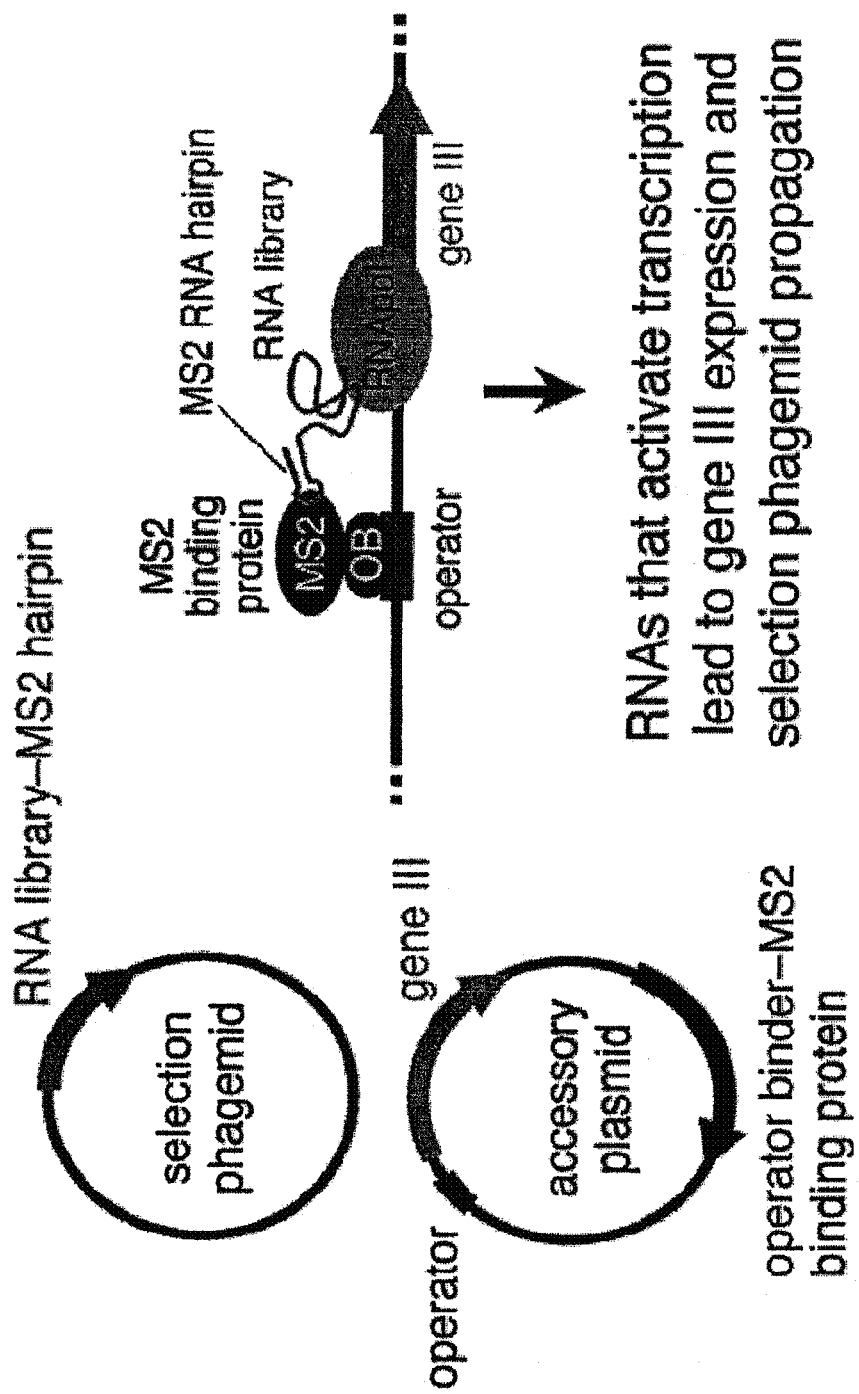
FIG. 6 illustrates the use of a generic selection phagemid and a generic accessory phagemid to evolve gene III.

The evolution of zinc-finger-targeted recombinase enzymes can proceed in an analogous manner. An example of the evolution can be seen in FIG. 6, where the selection phagemid for recombinase evolution is pRec-Sel which expresses a zinc-finger library fused with the Hin recombinase variant exemplifed in the results (Example 2). The accessory plasmid for recombinase evolution is pRec-Acc (FIG. 6), which contains desired recombination target sites positioned such that their recombination inverts a portion of the accessory plasmid. Inversion places a promoter in the correct orientation to drive gene III transcription. In contrast, recombination using non-target sites can result in excision of the promoter, preventing gene III expression. The combination of selection phagemid and accessory plasmid can simultaneously apply evolutionary pressure favoring desired recombinase specificity and disfavoring undesired specificity. In addition, recombinase evolution does not demonstrate premature expression due to incorporation of an inversion-based off-to-on selection. Importantly, the present invention enables the simultaneous evolution of many important and potentially interacting properties including protein stability, DNA-binding affinity, catalytic activity at target sites, and non-activity at undesired sites.

For both zinc finger and recombinase evolution, low selection stringency can be imposed initially using a strong RBS for an extended time, such as 24 hours (the equivalent of ~100 rounds of conventional directed evolution), to promote horizontal exploration of sequence space. Then the selection stringency can be raised successively, ending with a "summit-finding" high-stringency (weak RBS) accessory plasmid. The initial mutation rate can be set to a relatively high level, such as ~5×10$^{-3}$ mutations per phagemid replication event, and decrease mutation rate successively as selection stringency is elevated. The phagemid population can be sampled periodically, and the activity of encoded library members can be evaluated using a reporter construct. Reporter constructs can be similar to the accessory plasmid but containing a reporter gene, such as lacZ, in place of the propagation component. Standard LacZ blue/white screening can be used to identify colonies containing successful recombinases. The activities of evolved zinc-finger-targeted recombinase enzymes can be characterized in vivo and in vitro using established methods.

The recombinases emerging from continuous evolution, like the parental Hin recombinase, can be selected to be active as dimers. For example, homodimers can target sequences of the format [nine-base sequence]-$N_9$-RWWY-$N_9$-[nine-base reverse complement], where N=A, C, T, or G; R=A or G; Y=C or T; and W=A or T. However, any two evolved zinc-finger recombinases can form heterodimers to recombine target DNA sequences of the format $X_9$-$N_9$-RWWY-$N_9$-$Z_9$, where $X_9$ and $Z_9$ are two different nine-nucleotide sequences. The rarity of two such recognition sequences occurring as set distance apart, such as exactly 22 base pairs apart (one in 10$^{12}$ random base pairs), is sufficient to target a single site in a mammalian genome. In addition, this extreme target sequence rarity can also indicate that substrates for homodimeric recombinases rarely occur by chance in a genome, and therefore heterodimeric recombinases can be used without the need to preclude homodimerization. Importantly, even though any individual recombinase can be highly specific, a potential recognition site (RWWY) suitable for zinc-finger recombinase evolution occurs an average of once every 16 base pairs.

E. Analysis of Continuous Evolution System

The continuous evolution system described above is designed to allow phage propagation only as a result of library member-mediated propagation component expression. Mutagenesis takes place on a cellstat-wide basis and therefore can affect not only the genes encoding library members but also (i) the host cell genome; (ii) the accessory plasmid; (iii) the helper phagemid; and (iv) non-library-encoding regions of the selection phagemid. Design features of the continuous evolution system of the present invention minimizes the ability of each of these factors to influence selection phagemid propagation.

Because host cells flow through the cellstat faster than they (but not their infecting phage) can replicate, mutations in a particular host cell's genome cannot propagate during continuous evolution and can only influence phagemid propagation for a brief period. Likewise, because fresh accessory plasmid is provided by each fresh host cell, accessory plasmid mutations (such as those that elevate gene III transcription) also cannot propagate and cannot influence the long-term survival of library members. Unlike the host cell genome and the accessory plasmid, the helper phagemid can be packaged and introduced into other cells. However, all fresh host cells come with "wild-type" helper phagemids, so the impact of any mutant helper phage will be immediately diluted. Furthermore, because the helper phagemid contains no portion of gene III and no significant regions of homology with the selection plasmid, helper phagemid mutations cannot by themselves enable the survival of unfit library members. Since regions of the selection phagemid not encoding library members will be subject to mutation, some selection phagemid-determined parameters may change during continuous evolution. For example, mutations promoting increased library member expression can impart a growth advantage. However, simply increasing the expression level of an inactive library member cannot lead to survival in the system, and therefore only functional library members will propagate despite potential differences in expression level.

In some embodiments, "parasitic" selection phagemids can be used that cannot produce a propagation component on their own but survive by exploiting the ability of other selection phagemids within the same host cell to generate the propagation component. Fortunately, production of some propagation components, such as g3p, inhibits infection by additional phages, and therefore a host cell carrying a phagemid enabling production of a propagation component is naturally resistant to parasitic incursion. In the event that this resistance is incomplete, a small sub-population of parasitic selection phagemids can benefit continuous evolution by allowing a small fraction of surviving sequences to migrate horizontally across the fitness landscape, so long as the majority of the surviving phagemids represent truly active library members. The dependence of parasitic selection phagemids on truly fit phagemids ensures that the former cannot exist without the latter.

In summary, carefully designed selection phagemids and accessory plasmids are used to apply continuous directed evolution to the rapid generation of zinc-finger DNA-binding domains and zinc-finger-targeted recombinase enzymes with tailor-made sequence specificities.

One skilled in the art will appreciate further features and advantages of the invention based on the above-described embodiments. Accordingly, the invention is not to be limited by what has been particularly shown and described, nor by the examples set forth below, except as indicated by the appended claims. All publications and references cited herein are expressly incorporated herein by reference in their entirety.

EXAMPLES

This invention is further illustrated by the following examples which should not be construed as limiting. The following experiments were performed to demonstrate various aspects of the invention.

Example 1: Design and Testing of a Continuous Directed Evolution System

Figure 7:
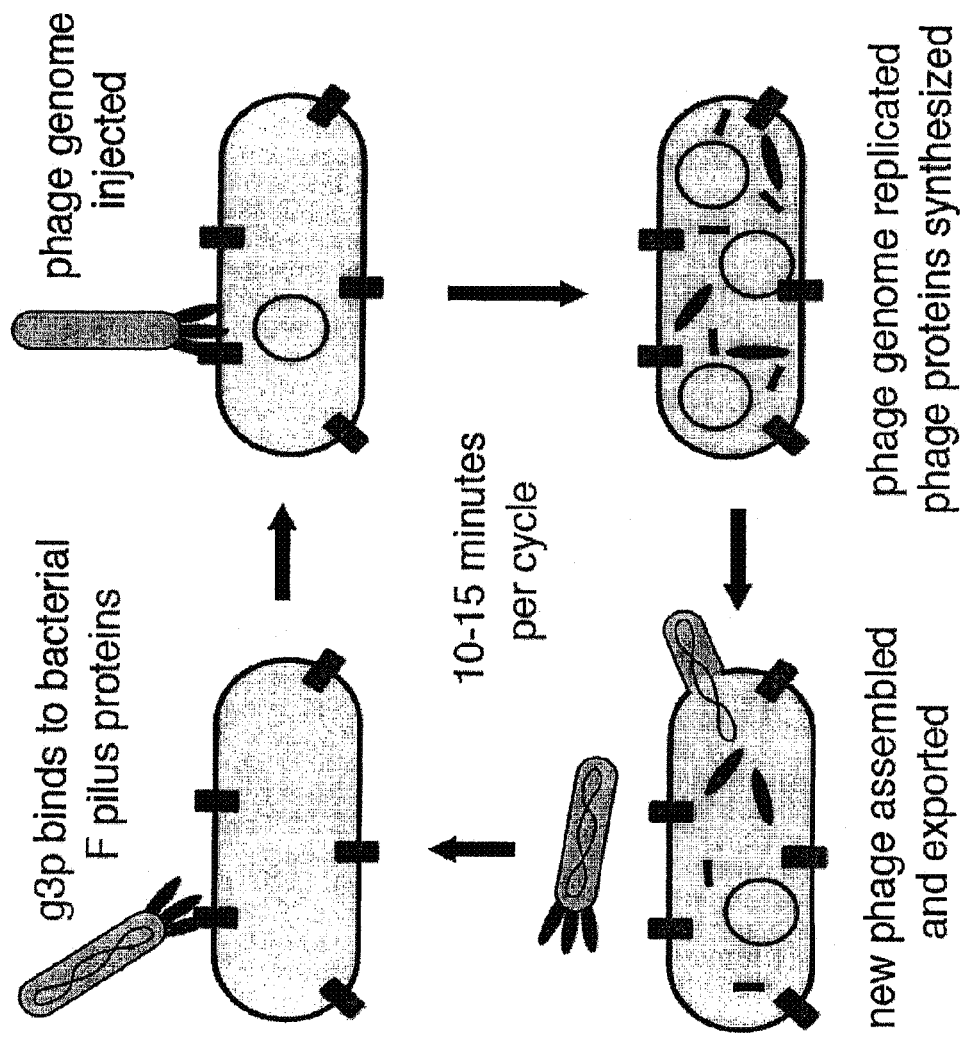
FIG. 7 depicts the life cycle of the filamentous bacteriophage.

The life cycle of the filamentous bacteriophage (FIG. 7) represents an ideal framework for a general continuous directed evolution system. Filamentous phages do not lyse their hosts; instead, the host bacterium continuously secretes phages at the cost of reduced host cell growth rate. Infection requires the phage gene III protein (g3p) to contact the F pilus and TolA receptor of a host cell. Phage unable to produce g3p are $\geq 10^9$-fold less infectious than wildtype phage.

Figure 8:
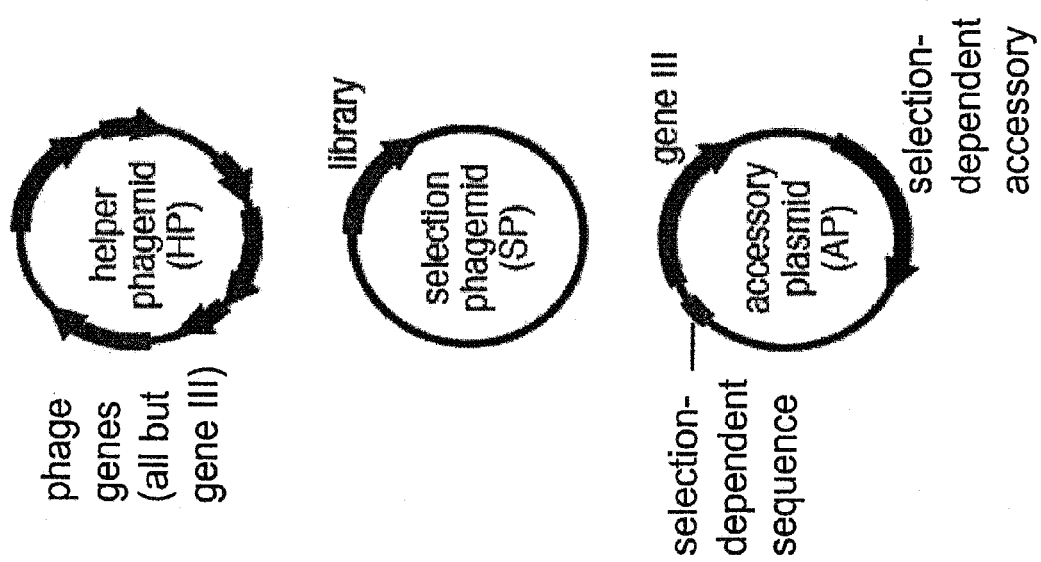
FIG. 8 depicts the continuous evolution system with four biological components: (i) a host *E. coli* cell (not shown); (ii) a helper phagemid (HP), present in all host cells, encoding all phage proteins except g3p; (iii) an accessory plasmid (AP), present in all host cells, that expresses gene III in response to an active library member; and (iv) a selection phagemid (SP) expressing the library of proteins or nucleic acids being evolved, which is replicated and packaged into secreted phage particles.
Figure 9:
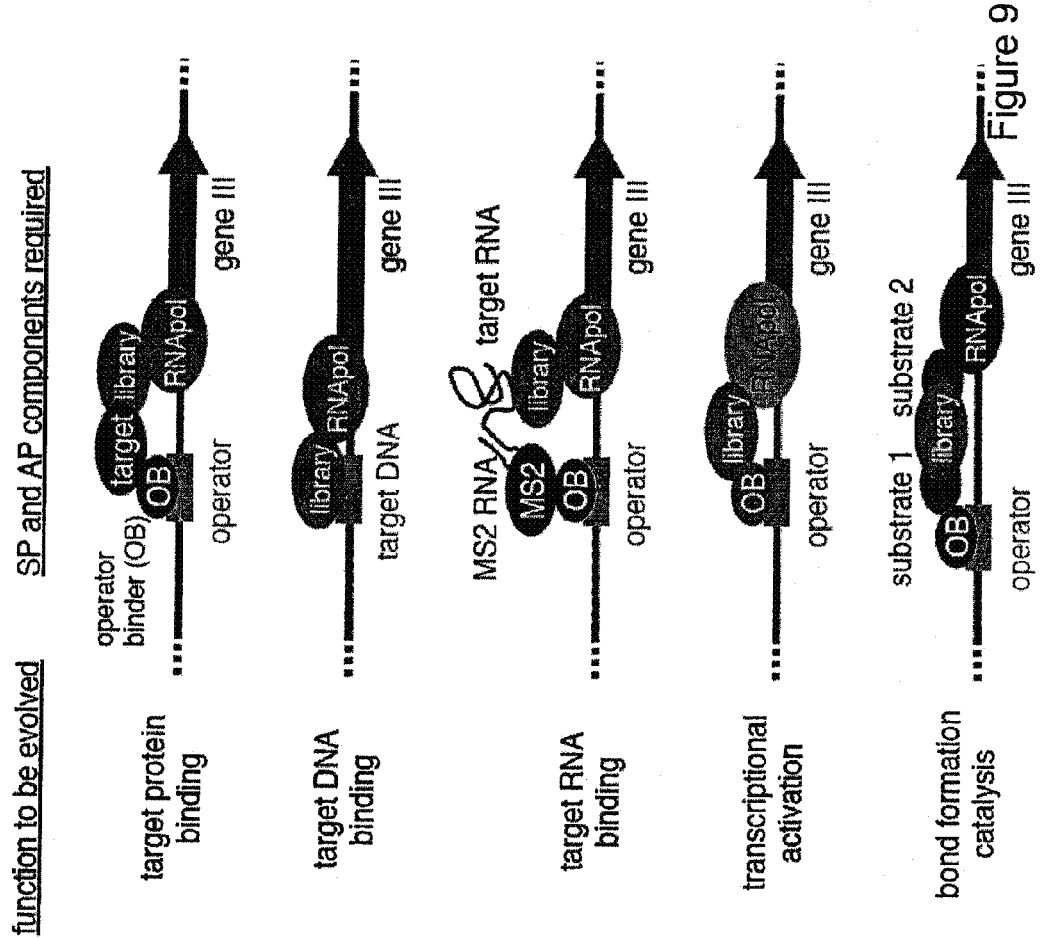
FIG. 9 depicts different protein or nucleic acid activities linked to gene III and capable of being evolved.

The continuous evolution system of the present invention comprises four biological components: (i) a host *E. coli* cell; (ii) a "helper phagemid", present in all host cells, encoding all phage proteins except g3p; (iii) an "accessory plasmid", present in all host cells, that expresses gene III in response to an active library member; and (iv) a "selection phagemid" expressing the library of proteins or nucleic acids being evolved, which is replicated and packaged into secreted phage particles (FIG. 8). In addition, helper and accessory plasmids can be combined into a single plasmid. New host cells can only be infected by phage particles that contain g3p. Fit selection phagemids encode library members that induce g3p expression from the accessory plasmid and are therefore packaged into phage particles that contain g3p. These g3p containing phage particles can infect new cells, leading to further replication of the fit selection phagemids (FIG. 9). In contrast, low-fitness selection phagemids encode library members incapable of inducing g3p expression and are packaged into phage particles lacking g3p. These g3p-deficient phage particles are non-infectious, and therefore low-fitness selection phagemids cannot propagate. Because gene III expression can be linked to a range of protein binding, nucleic acid binding, or reaction catalysis events using many previously developed n-hybrid strategies, this system has the potential to be applicable to a wide variety of protein or nucleic acid activities of interest (FIG. 9).

Figure 2:
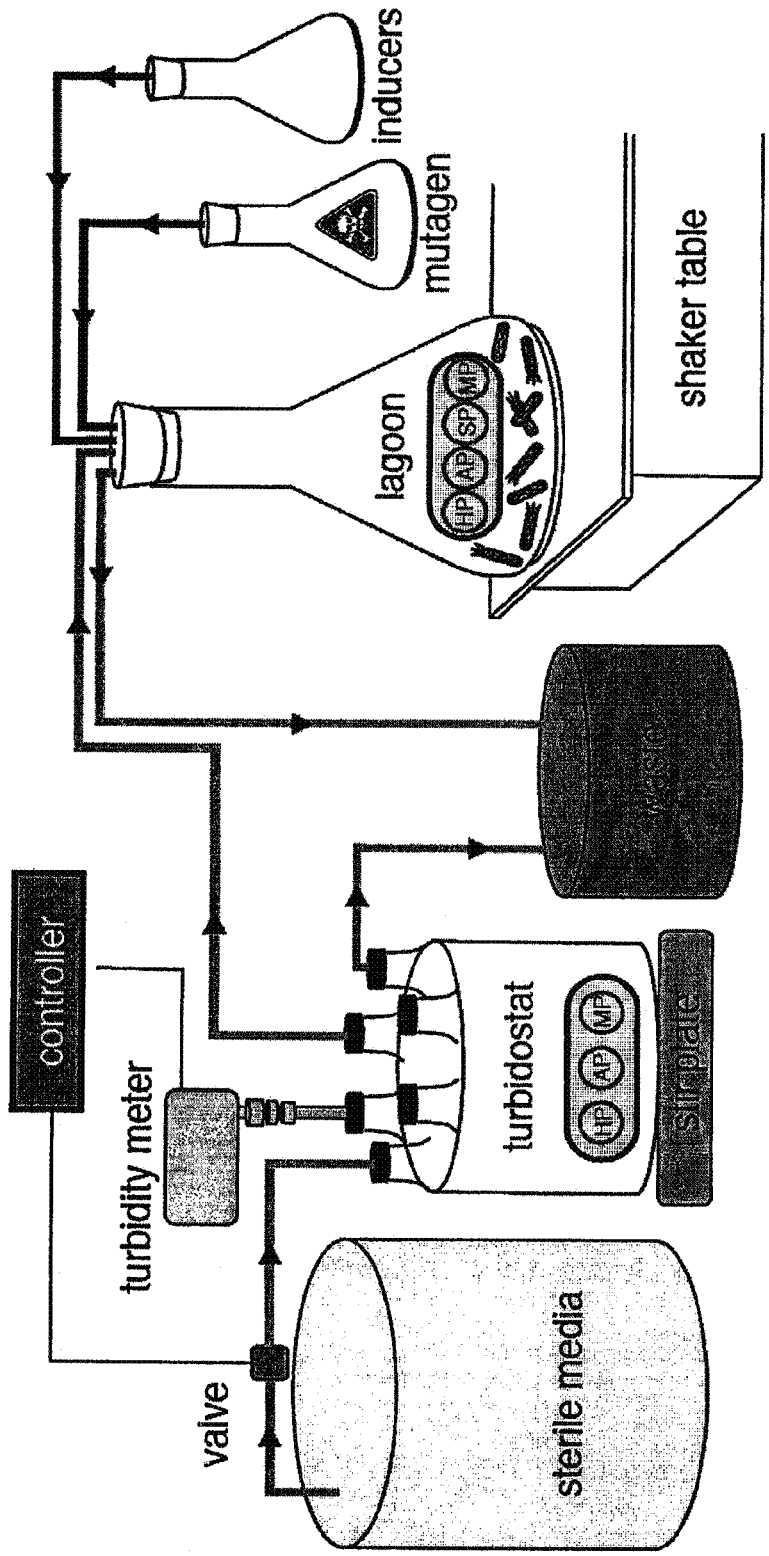
FIG. 2 depicts the cellstat, a culture vessel interfaced with a system of automated valves, within which continuous evolution can take place. The cellstat receives a constant supply of uninfected host cells from a host cell culture maintained at a constant cell density of $2\times10^8$ cells/mL (the "turbidostat"), as well as chemical mutagen in liquid form.

To implement this system a "cellstat" was constructed, consisting of a culture vessel interfaced with a system of automated valves, within which continuous evolution can take place. The cellstat receives a constant supply of uninfected host cells from a host cell culture maintained at a constant cell density of $2 \times 10^8$ cells/mL (the "turbidostat"), as well as chemical mutagen in liquid form (FIG. 2). The cellstat also drains to waste so that its volume remains constant. Within the cellstat, selection phagemids encoding fit proteins or nucleic acids are constantly replicating, infecting fresh host cells, and mutating, while unfit selection phagemids do not replicate and are quickly lost to waste. The cellstat therefore serves several key functions: (i) it provides the environment in which phagemids containing evolving library sequences can replicate; (ii) it allows a chemical mutagen to continually diversify genes encoding library members; (iii) it supports selection phagemid propagation in a g3p-dependent manner, and (iv) it constantly dilutes the evolving culture with fresh host cells and media, removing unfit selection phagemids and old host cells in the process.

Figure 10:
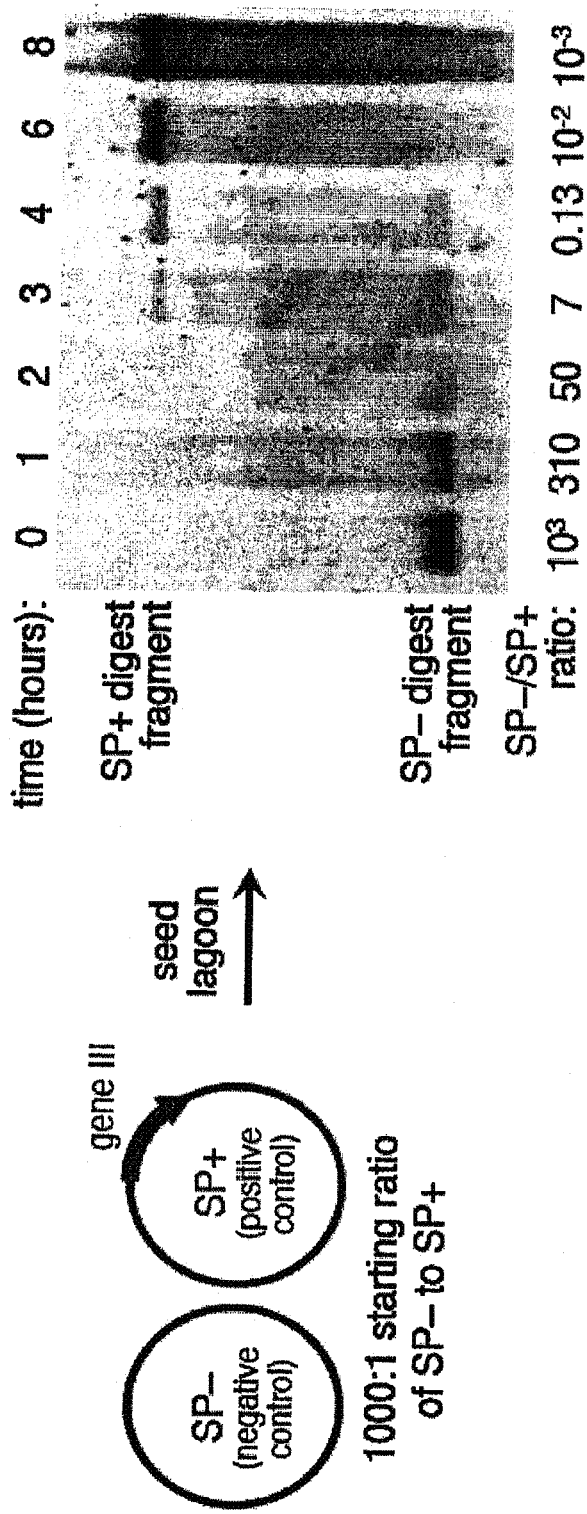
FIG. 10 shows the positive control mock-selection phagemid (SP+) that expresses gene III from a constitutive promoter, and a negative control selection phagemid that lacks gene III. The SP+ phagemid demonstrated a $10^6$ fold enrichment after 8 hours of continuous propagation.

The results demonstrate the ability of the cellstat to accomplish each of these four functions. A positive control mock-selection phagemid (SP+) that expresses gene III from a constitutive promoter, and a negative control selection phagemid that lacks gene III (FIG. 10) were constructed. Three cellstats were seeded with a 1000:1 ratio of SP− to SP+. Host *E. coli* cells maintained at early exponential growth phase in minimal media were pumped from the turbidostat into each cellstat at a dilution rate of 0.75 cellstat volumes per hour. The phagemids were continuously cultured for 24 hours, with a sample taken every hour and subjected to analysis by restriction digestion and DNA sequencing of harvested selection phagemids. It was observed a steady decrease in SP− abundance at a rate consistent with the rate of dilution, such that after six hours no significant amount of SP− was detected by restriction digestion analysis. In contrast, the population of SP+ first became visible at three hours and grew steadily to represent >99% of the selection phagemids within 6-8 hours (FIG. 10). These results demonstrate that the cellstat system can continuously enrich a mixed phagemid population for initially rare members that express gene III, and that phagemids that do not lead to g3p production are efficiently lost by continuous dilution.

In order to test the ability of the system to continuously mutagenize a gene pool, the cellstats containing the SP+ phagemid were exposed to 0.5 mM of the chemical mutagen methyl methane sulfonate (MMS), a concentration predicted to induce significant mutagenesis but that enables most host cells to survive for the ~15 min duration needed to replicate and export phage. In addition, a diversification plasmid was used with MMS due to the time required for induction of the natural SOS response. After varying lengths of time up to 24 hours, phagemids were isolated and subjected to DNA sequencing. Sequences corresponding to an average mutagenesis rate of 0.1%-0.3% per base pair per hour of cellstat culture were observed in non-essential regions of the selection phagemid, with progressively longer incubation times resulting in a greater mutation frequency (Table 1). In contrast, no mutations were observed in essential regions of gene III or in the antibiotic resistance gene ($kan^r$) required for selection phagemid isolation. Furthermore, it was observed that no mutations from selection phagemids were grown in cellstats lacking MMS after 24 h (Table 1). These results demonstrate the ability of the cellstat to support the continuous diversification of a cellstat culture phagemid population through chemical mutagenesis.

TABLE 1

Mutation frequency corresponding to time in culture

| [MMS] (mM) | cellstat culture time (h) | % mutations in non-essential DNA |
|---|---|---|
| 0.5 | 0 | 0% |
| 0.5 | 1 | 0.3% |
| 0.5 | 4 | 0.6% |
| 0.5 | 8 | 0.9% |
| 0.5 | 24 | 2.0% |
| 0 | 24 | 0% |

Example 2: Evaluation of Recombinase Suitability for Continuous Evolution

Figure 11:
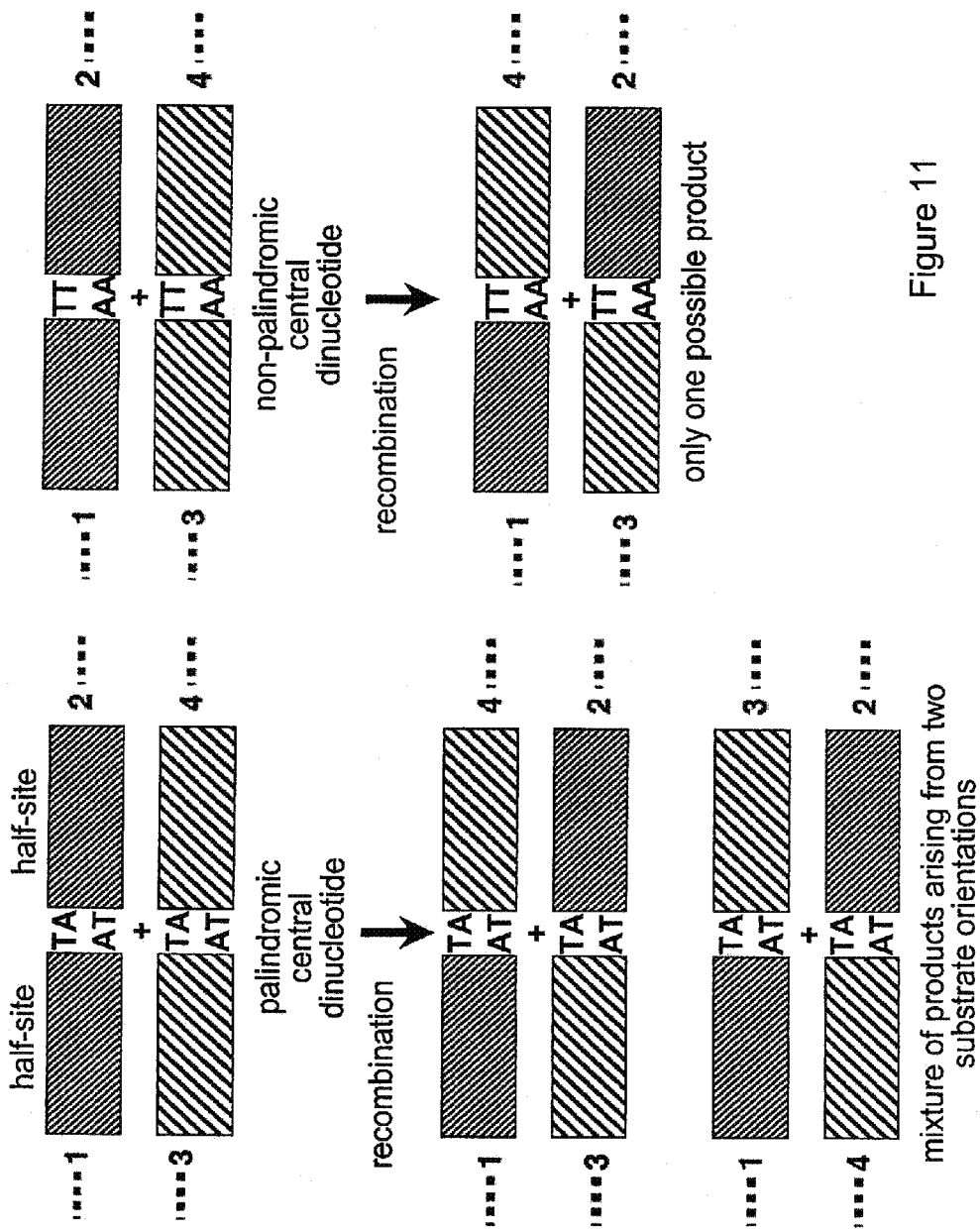
FIG. 11 depicts the resulting sequence combination products after recombination by a recombinase enzyme that recognizes a central dinucleotide sequence that is palindromic or non-palindromic.

Recombinases of the Tn3 serine recombinase family naturally bind to their recognition sites as dimers, with the catalytic domains dimerizing at the central dinucleotide cleaved during recombination. Replacing the native Tn3 DNA-binding domain with the Zif268 zinc finger results in recombinase recognition of half-sites consisting of the nine nucleotides bound by Zif268, followed by a ten-nucleotide region inherited from the Tn3 recognition sequence and the central dinucleotide. However, it is not known how many of the ten inherited nucleotides flanking the central dinucleotide are required for Tn3 activity. A recombinase enzyme ideally suited for targeting with evolved zinc-finger domains should have minimal sequence requirements other than the zinc-finger programmed sequence flanking the central dinucleotide. In addition, to control the orientation with which recombination takes place, the central dinucleotide recognized by the enzyme should ideally be non-palindromic (FIG. 11). While Tn3 recombinase naturally recognizes a palindromic TA central dinucleotide, the closely related Hin recombinase naturally operates on non-palindromic AA or TT central dinucleotides, enabling orientation-specific recombination. To evaluate the suitability of Hin recombinase as a starting point for the directed evolution efforts, a chimeric Zif268-Hin recombinase was generated and its DNA sequence requirements characterized among the ten nucleotides between the Zif268 recognition sequence and the central dinucleotide.

A Zif268-targeted Hin recombinase was created by linking the catalytic domain of hyperactive Hin (H107Y, amino acids 1-141) to Zif268 by a flexible linker of sequence GSGGSGGSGGSGTS (SEQ ID NO: 1). Induction of Zif268-Hin expression led to recombination of recognition sites analogous to those of the Stark experiment, inverting the DNA sequence between two oppositely oriented sites. To confirm inversion, recombined plasmids were purified and sequenced.

Then a library was generated consisting of all possible intervening sequences within a Zif268-Hin DNA recombination site by randomizing the ten base pairs between the zinc-finger binding site and the central dinucleotide of the recognition half-site (FIG. 4). In order to identify library members that are substrates for the Zif268-Hin recombinase, a PCR-based selection to amplify only the recombined sites was used. The substrate plasmid contains PCR primer-binding sites on the same strand, preventing amplification by PCR. Successful recombination inverts one of the primer-binding sites, enabling PCR amplification of the recombined site (FIG. 4). This simple PCR-based selection was applied to the library of possible Zif268-Hin recombination sites. A comparison of DNA sequences from the library before and after selection resulted in a sequence logo of Zif268-Hin sequence tolerance (FIG. 4).

The results revealed that the enzyme displays minimal sequence requirements between the Zif268 recognition site and the central dinucleotide, except that the nucleotide (base 10) immediately flanking the cleavage site must be a purine. These minimal requirements of—RWWY—(where R=A or G, W=A or T, and Y=T or C) establish zincfinger-targeted Hin as a promising starting point for the continuous evolution of site-specific recombinases capable of targeting a wide range of DNA sequences.

In summary, the features of the filamentous bacteriophage life cycle and simple automated liquid handling technologies were exploited to design a system capable of supporting continuous evolution. The results establish the ability of the cellstat system to continuously perform diversification, selection, and amplification in a g3p-dependent manner. In addition, the suitability of a Hin recombination variant for the continuous evolution of zinc-finger-targeted recombinase enzymes was confirmed with virtually any sequence specificity.

All publications and references are herein expressly incorporated by reference in their entirety. The terms "a" and "an" can be used interchangeably, and are equivalent to the phrase "one or more" as utilized in the present application. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An apparatus for continuous evolution of a gene of interest, the apparatus comprising
   (a) a cellstat comprising
      (i) a cell culture vessel comprising a population of host cells wherein the host cells comprise phage genes required to package a selection phagemid into infectious phage particles,
      (ii) a population of phages comprising the gene of interest to be evolved, wherein the population of phages is capable of infecting the host cells and introducing the gene of interest to be evolved into the host cells, wherein at least one of the phage genes required to package the selection phagemid into infectious phage particles is expressed in response to expression of the gene of interest to be evolved in the host cells;
      (iii) an inflow connected to a turbidostat;
      (iv) a drain to waste;
      (v) a pump effecting a flow of host cells through the cellstat, wherein the flow rate of the host cells through the cellstat permits replication of the phage, but not of the host cells, in the cellstat; and
   (b) a turbidostat comprising
      (i) a population of uninfected host cells maintained at a substantially constant cell density; and
      (ii) an outflow connected to the inflow of the cellstat.

2. The apparatus of claim 1, wherein the apparatus further comprises
   (c) a vessel comprising a mutagen in liquid form.

3. The apparatus of claim 1, wherein the phages are filamentous phages.

4. The apparatus of claim 1, wherein the phages are M13 phages.

5. The apparatus of claim 1, wherein the selection phagemid comprises the at least one phage gene required to package the selection phagemid into infectious phage particles.

6. The apparatus of claim 1, wherein the host cells comprise:
   a helper plasmid comprising a phage genome in which at least one gene required to package the selection phagemid into phage particles is disabled; and
   an accessory plasmid comprising the gene required to package the selection phagemid into phage particles that is disabled in the helper plasmid, wherein the gene is expressed from the accessory plasmid in response to expression of the gene to be evolved.

7. The apparatus of claim 6, wherein the gene required to package the selection phagemid into phage particles is gene II protein (g2p), gene III protein (g3p), or gene VI protein (g6p).

8. The apparatus of claim 6, wherein the phage genome is selected from the group consisting of an M13 phage genome, an fd page genome, an f1 phage genome, a ZJ/2 phage genome, an Ec9 phage genome, an AE2 phage genome, an HR phage genome, a δA phage genome, and an Ike phage genome.

9. The apparatus of claim 2, wherein said mutagen is selected from the group consisting of nucleotide analogues, nucleoside precursors, alkylating agents, cross-linking agents, genotoxins, and radiation.

10. The apparatus of claim 2, wherein said mutagen is a chemical mutagen.

11. The apparatus of claim 10, wherein said chemical mutagen is selected from the group consisting of 3-Chloro-4-(dichloromethyl)-5-hydroxy-2(5H)-furanone (MX) (CAS no. 77439-76-0), O,O-dimethyl-S-(phthalimidomethyl) phosphorodithioate (phos-met) (CAS no. 732-11-6), formaldehyde (CAS no. 50-00-0), 2-(2-furyl)-3-(5-nitro-2-furyl) acrylamide (AF-2) (CAS no. 3688-53-7), glyoxal (CAS no. 107-22-2), 6-mercaptopurine (CAS no. 50-44-2), N-(trichloromethylthio)-4-cyclohexane-1,2-dicarboximide (captan) (CAS no. 133-06-2), 2-aminopurine (CAS no. 452-06-2), methyl methane sulfonate (MMS) (CAS No. 66-27-3), 4-nitroquinoline 1-oxide (4-NQO) (CAS No. 56-57-5), N4-Aminocytidine (CAS no. 57294-74-3), sodium azide (CAS no. 26628-22-8), N-ethyl-N-nitrosourea (ENU) (CAS no. 759-73-9), N-methyl-N-nitrosourea (MNU) (CAS no. 820-60-0), 5-azacytidine (CAS no. 320-67-2), cumene hydroperoxide (CHP) (CAS no. 80-15-9), ethyl methanesulfonate (EMS) (CAS no. 62-50-0), N-ethyl-N-nitro-N-nitrosoguanidine (ENNG) (CAS no. 4245-77-6), N-methyl-N-nitro-N-nitrosoguanidine (MNNG) (CAS no. 70-25-7), 5-diazouracil (CAS no. 2435-76-9) and t-butyl hydroperoxide (BHP) (CAS no. 75-91-2).

12. The apparatus of claim 1, wherein the host cells are engineered to inducibly express SOS mutagenizing lesion-bypass proteins.

13. The apparatus of claim 12, wherein the SOS mutagenizing lesion-bypass proteins are selected from the group consisting of polymerase V and activated recA.

14. The apparatus of claim 1, wherein the host cells comprise a mutagenic plasmid capable of inducibly expressing an error-prone DNA polymerase subunit.

15. The apparatus of claim 14, wherein the apparatus comprises a vessel comprising an agent inducing expression of the SOS mutagenizing lesion-bypass proteins from the mutagenic plasmid.

16. The apparatus of claim 15, wherein the agent inducing expression of the SOS mutagenizing lesion-bypass proteins from the mutagenic plasmid is arabinose.

17. The apparatus of claim 6, wherein a gene required to package the selection phagemid into phage particles that is disabled in the helper plasmid is inducibly expressed from the accessory plasmid.

18. The apparatus of claim 1, wherein the host cells comprise a system of transferring nucleic acids from one cell to another via phage infection.

19. The apparatus of claim 4, wherein the M13 phages do not comprise a full-length pIII gene.

20. The apparatus of claim 1, wherein the host cells are prokaryotic cells amenable to phage infection, replication, and production.

21. The apparatus of claim 1, wherein the host cells are *E. coli* cells.

* * * * *

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic polypeptide

```
<400> SEQUENCE: 1

Gly Ser Gly Gly Ser Gly Gly Ser Gly Gly Ser Gly Thr Ser
1               5                   10
```